United States Patent
Mensah

(10) Patent No.: US 10,010,084 B2
(45) Date of Patent: *Jul. 3, 2018

(54) CONTROL OF INSECT PESTS

(71) Applicant: INNOVATE AG PTY LIMITED, Wee Waa (AU)

(72) Inventor: Robert Mensah, Narrabri (AU)

(73) Assignee: INNOVATE AG PTY LIMITED, Wee Waa (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,621

(22) Filed: Nov. 25, 2015

(65) Prior Publication Data

US 2016/0174571 A1 Jun. 23, 2016

Related U.S. Application Data

(63) Continuation of application No. 13/880,656, filed as application No. PCT/AU2012/000160 on Feb. 21, 2012, now Pat. No. 9,271,503.

(30) Foreign Application Priority Data

Feb. 21, 2011 (AU) .............................. 2011900586

(51) Int. Cl.
| | | |
|---|---|---|
| A61K 36/00 | (2006.01) | |
| A01N 65/20 | (2009.01) | |
| A61K 36/48 | (2006.01) | |
| A01N 65/00 | (2009.01) | |

(52) U.S. Cl.
CPC ............. *A01N 65/20* (2013.01); *A01N 65/00* (2013.01); *A61K 36/48* (2013.01)

(58) Field of Classification Search
CPC .................................................... A61K 36/00
See application file for complete search history.

(56) References Cited

U.S. PATENT DOCUMENTS

| | | |
|---|---|---|
| 9,271,503 B2 | 3/2016 | Mensah |
| 2008/0003197 A1 | 1/2008 | Bette |
| 2008/0193387 A1 | 8/2008 | De Wolff |
| 2013/0052282 A1 | 2/2013 | Saunders et al. |

FOREIGN PATENT DOCUMENTS

| | | | | |
|---|---|---|---|---|
| JP | 2007016003 A | * | 1/2007 | |
| JP | 2008162897 A | * | 7/2008 | |
| WO | WO-2005/034631 A2 | | 4/2005 | |
| WO | WO 2005034631 A2 | * | 4/2005 | ............. A01N 27/00 |
| WO | WO-2012/113017 A1 | | 8/2012 | |

OTHER PUBLICATIONS

Mathew et al, Larvicidal activity of Saraca indica, Nyctanthes arbor-tristis, and Clitoria ternatea extracts against three mosquito vector species. Parasitology research, (Apr. 2009) vol. 104, No. 5, pp. 1017-1025.*
Taur et al, Phytochemical investigation and evaluation of Clitoria ternatea seeds extracts on clonidine induced catalepsy in mice. Pharmacologyonline (2009), (3, News Letters), 215-220.*
Bernays, E.A., et al. "Host plant selection by phytophagous insects." Chapman and Hall. London (1994).
Kelemu, S., et al. "Antimicrobial and insecticidal protein isolated from seeds of Clitoria ternatea, a tropical forage legume," Plant Physiology and Biochemistry, vol. 42, pp. 867-873 (2004).
Mathew et al, Larvicidal activity of Saraca indica, Nyctanthes arbor-tristis, and Clitoria ternatea extracts against three mosquito vector species.Parasitology research, (Apr. 2009) vol. 104, No. 5, pp. 1017-1025.
Mathew, N., et al. "Larvicidal activity of Saraca indica, Nyctanthes arbor-tristis, and Clitoria ternatea extracts against three mosquito vector species," Parasitol Res, vol. 104, pp. 1017-1025 (2009).
Mensah, R.K., et al. "A review of behavior modifying chemicals in relation to pest host selection and management on australian cottons." CRDC (1999).
Mensah, R.K., et al. "Deterrence of oviposition of adult ostrinia nubilalis (hubner) by a natural enemy food supplement Envirofeast. RTM. on maize in France." International Journal of Pest Management, vol. 46(1), pp. 49-53 (2000).
Mensah, R.K., et al. Suppression of *Helicoverpa* spp. Oviposition by use of natural enemy food supplement "Envirofeast." Australian Journal of Entomology, vol. 35, pp. 323-329 (1996).
Miller, J.R., et al. "Stimulo-deterrent diversion: a concept and its possible application to onion maggot control." J. Chem. Ecol. vol. 16, pp. 3197-3212 (1990).
Nityanathasiddhah, "Laksadivati/dhupah (rasendrasarasamgrahah)," Rasaratnakarah-Rasendra khandam, TKDL Abstract No. AK/1026, Knowledge known for 500 years abstract, 2012.
"Astasugandhadhupah," Nighanturatnakarah, TKDL Abstract No. RG/3942, Knowledge known for 50 years abstract, 2012.
Pandey et al., "Antifeeding, Repellent and Insecticidal Efficacy of Plant Products Against Helicoverpa Armigera," Annals of Plant Protection Sciences, 2010, 18(2) 304-306.
Pyke, B., et al. "The push-pull strategy-behavioural control of heliothis." Australian Cotton Grower, vol. 9, pp. 7-9 (1987).
Rhoades, D.F., et al. "Toward a general theory of plant antiherbivore chemistry." In: J.W. Wallace and L. Mansell, eds. Biochemical Interactions Between Insects and Plants. New York, pp. 168-213 (1976).
Tingle, F.C., et al. Aqueous extracts from indigenous plants as oviposition deterrents for heliothis virescens. J. Chem. Ecology, vol. 10, pp. 101-113 (1984).
International Search Report and Written Opinion dated Mar. 26, 2012 for International Patent Application No. PCT/AU2012/000160, which was filed on Feb. 21, 2012 and published as WO 2012/113017 on Aug. 30, 2012 (Inventor—Mensah //Applicant—Innovate Ag Pty Limited) (8 pages).

(Continued)

*Primary Examiner* — Qiuwen Mi

(74) *Attorney, Agent, or Firm* — Ballard Spahr LLP

(57) ABSTRACT

A composition for controlling insect pests comprising an extract from *Clitoria ternatea* comprising SPCs which have insecticidal activity and/or which repel the insect pest and/or deter the insect pest from laying eggs and/or influence the position of egg laying and/or deter the insect pest from feeding on a plant, wherein the composition optionally comprises a carrier.

22 Claims, 10 Drawing Sheets

(56) References Cited

OTHER PUBLICATIONS

International Preliminary Report on Patentability dated Apr. 2, 2013 for International Patent Application No. PCT/AU2012/000160, which was filed on Feb. 21, 2012 and published as WO 2012/113017 on Aug. 30, 2012 (Inventor—Mensah //Applicant—Innovate Ag Pty Limited) (7 page).
Non-Final Office Action dated May 16, 2014 for U.S. Appl. No. 13/880,656, filed Apr. 19, 2013 and granted as U.S. Pat. No. 9,271,503 on Mar. 1, 2016 (Inventor—Mensah) (9 pages).
Response to Non-Final Office Action filed on Oct. 15, 2014 for U.S. Appl. No. 13/880,656, filed Apr. 19, 2013 and granted as U.S. Pat. No. 9,271,503 on Mar. 1, 2016 (Inventor—Mensah) (13 pages).
Final Office Action dated Oct. 22, 2014 for U.S. Appl. No. 13/880,656, filed Apr. 19, 2013 and granted as U.S. Pat. No. 9,271,503 on Mar. 1, 2016 (Inventor—Mensah) (12 pages).
Response to Final Office Action filed on Mar. 23, 2015 for U.S. Appl. No. 13/880,656, filed Apr. 19, 2013 and granted as U.S. Pat. No. 9,271,503 on Mar. 1, 2016 (Inventor—Mensah) (16 pages).
Non-Final Office Action dated May 13, 2015 for U.S. Appl. No. 13/880,656, filed Apr. 19, 2013 and granted as U.S. Pat. No. 9,271,503 on Mar. 1, 2016 (Inventor—Mensah) (12 pages).
Response to Non-Final Office Action filed on Aug. 13, 2015 for U.S. Appl. No. 13/880,656, filed Apr. 19, 2013 and granted as U.S. Pat. No. 9,271,503 on Mar. 1, 2016 (Inventor—Mensah) (10 pages).
Notice of Allowance dated Aug. 25, 2015 for U.S. Appl. No. 13/880,656, filed Apr. 19, 2013 and granted as U.S. Pat. No. 9,271,503 on Mar. 1, 2016 (Inventor—Mensah) (7 pages).

* cited by examiner

CONTROL OF INSECT PESTS

CROSS REFERENCE TO RELATED APPLICATIONS

The present application is a continuation of U.S. application Ser. No. 13/880,656 filed on Apr. 19, 2013, which is a U.S. National Phase entry of International Application No. PCT/AU2012/000160, filed Feb. 21, 2012, which claims priority to Australian Patent Application No. 2011900586, filed Feb. 21, 2011; which all three prior applications are hereby incorporated herein by this reference in their entireties.

TECHNICAL FIELD

The present invention relates to the use *Clitoria ternatea* for the control of insect pests, more particularly to the control of moths and their and larvae, and chewing or sap sucking insects generally, through insecticidal activity and/or repelling the insect pest and/or deterring the insect pest from laying eggs and/or influencing the position of egg laying and/or deterring the insect pest from feeding on an agricultural crop or other plant. In particular, the present invention relates to the use of extracts from *Clitoria ternatea* for the control of insect pests of agricultural crops and other plants, more particularly to the control of moths and their larvae and chewing or sap sucking insects on agricultural crops and other plants.

BACKGROUND ART

The Australian cotton industry still relies on repeated applications of synthetic pesticides to manage pests in crops. Accompanying problems associated with insecticide resistance, disruption of beneficial species, high cost of production, and environmental impact now require that alternative strategies be investigated for managing *Helicoverpa* spp. These include (but are not limited to) genetically engineered cotton crops containing insecticidal protein of *Bacillus thuringiensis* (Bt) and other host plant resistances, biopesticides, better management of beneficial species, trap crops, intercropping and companion planting, and manipulation of the behaviour of pests and beneficial insects. Genetically engineered (transgenic) crops are now grown in Australia and many countries to control lepidopteran pests and their introduction has reduced synthetic insecticide use against these pests. However, other pests are not affected by the toxin in the transgenic plants e.g. sucking pests. Also third to late stage *Helicoverpa* larvae that can tolerate the toxin have led to increased use of synthetic insecticides to control them on both transgenic and conventional cotton crops. Thus the need to develop new approaches to manage these pests is crucial.

One of the approaches with greater potential to revolutionalise the way insect pests are managed in broadacre crops such as cotton, is the use of natural plant chemical compounds or plant extracts. The natural plant extracts or secondary plant compounds (SPCs) in general can influence the behaviour of insects by functioning as cues stimulating an insect's "interest" or deter insects from infesting a particular host plant (Rhoades and Coates 1976). Many SPCs have evolved in plants to actually protect the plants against pest infestation (Rhoades and Coates 1976). This has led to several examples of SPCs being used as botanical insecticides to reduce pest damage when applied to crop plants. Some SPCs extracted from non-host plants and then sprayed on host plants can change the behaviour of a pest, particularly moths, which then avoid the host plant (Tingle and Mitchell 1984). Numerous studies into pest management have focussed on chemical compounds that kill the pest rather than behaviour modifying compounds (Tingle and Mitchell 1984, Mensah and Moore, 1999). Consequently, potentially useful compounds with more subtle modes of action that could lead to novel products have been overlooked (Mensah and Moore, 1999). Such compounds attract or repel pests over considerable distances; or stimulate or deter both feeding and egg-laying following contact. Deterrent compounds directly suppress oviposition and feeding by insects (Mensah, 1996, Mensah et al. 2000), they are considered more important than stimulants and in fact a deterrent effect is more commonly noted in SPCs (Bernays and Chapman 1994). It is plausible that the efficacy of a deterrent would be increased when used in combination with an attractant/stimulant applied to a non-valued resource (Miller and Cowles, 1990) in a push-pull strategy (Pyke et al. 1987). Therefore, a tool to modify egg laying and/or feeding behaviour of insect pests is a novel approach to pest management in agricultural crops and offers potentially very significant benefits.

SUMMARY OF THE INVENTION

In one aspect the present invention provides a composition for controlling insect pests comprising an extract from *Clitoria ternatea* comprising SPCs which have insecticidal activity and/or which repel the insect pest and/or deter the insect pest from laying eggs and/or influence the position of egg laying and/or deter the insect pest from feeding on a plant, wherein the composition optionally comprises a carrier.

In a further aspect the present invention provides a method of controlling one or more insect pests, the method comprising treating a locus with an SPC having insecticidal activity and/or which repels the insect pest and/or which deters the insect pest from laying eggs and/or influences the position of egg laying and/or which deters the insect pest from feeding on a plant, and which is derived from *Clitoria ternatea*.

MOBILE PHASE: A=0.05% TRIFLUOROACETIC ACID (TFA)-WATER B=0.05% TFA-ACETONITRILE

Figure 1:
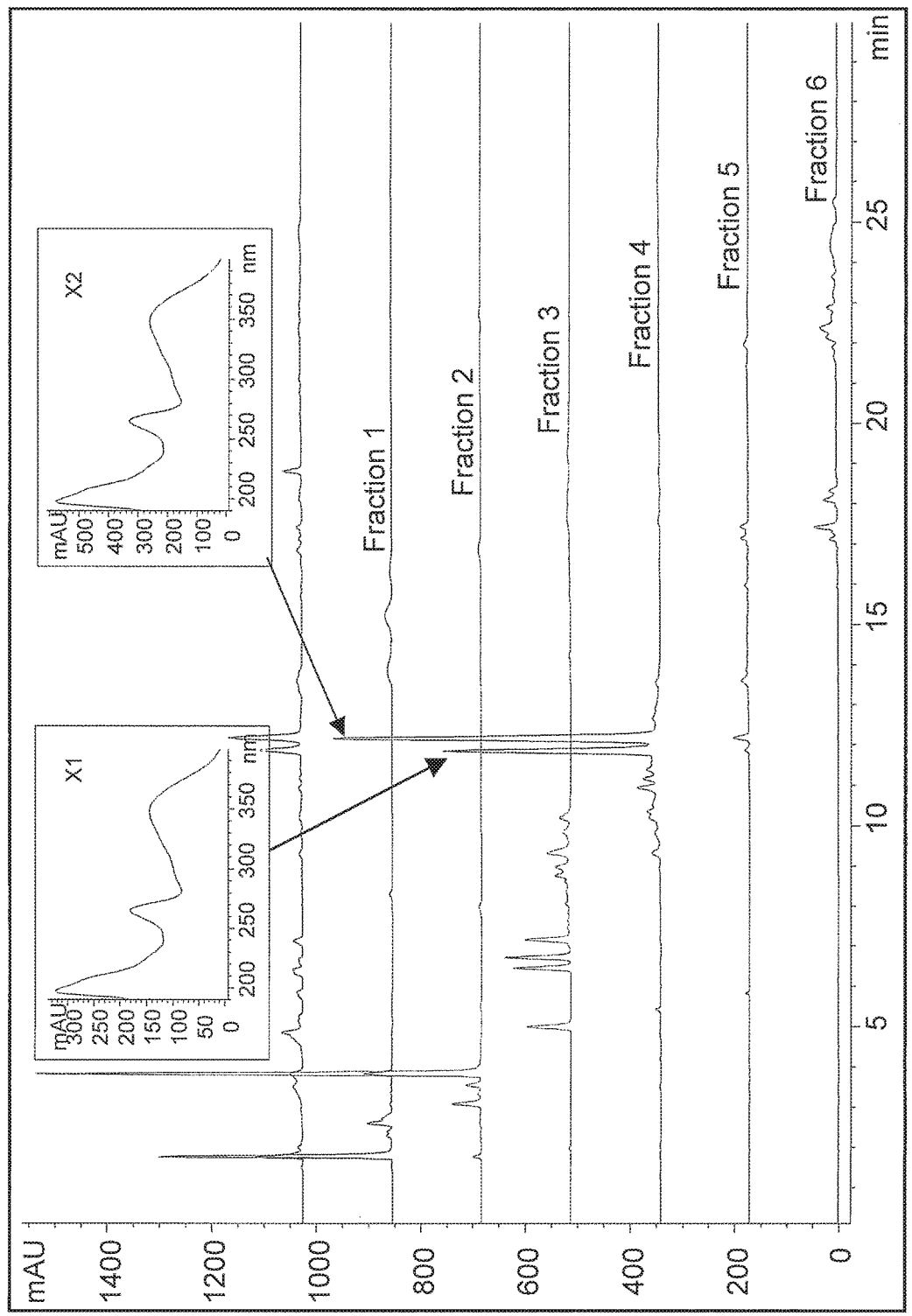
FIG. 1 shows HPLC chromatograms of solid phase extraction (SPE) fractions from *Clitoria ternatea* together with UV spectra.

| Time (min) | % A | % B | Flow rate (mL/min) |
|---|---|---|---|
| 0 | 90 | 10 | 1.0 |
| 17.5 | 80 | 20 | 1.0 |
| 20 | 5 | 95 | 1.0 |
| 22.5 | 5 | 95 | 1.0 |
| 25 | 90 | 10 | 1.0 |
| 30 | 90 | 10 | 1.0 |

DETAILED DESCRIPTION OF THE INVENTION

The present invention relates to the control of one or more insect pests with SPCs derived from *Clitoria ternatea*.

As used herein an SPC, or secondary plant compound, is chemical compound synthesised by a plant which is not essential to the survival of the plant. The SPCs of the present have insecticidal activity and/or repel the insect pest and/or deter the insect pest from laying eggs and/or influence the position of egg laying and/or deter the insect pest from feeding on the plant.

In an embodiment, the insect pest is a plant pest and the method comprises applying an extract from *Clitoria ternatea* to the plant or its surroundings.

Embodiments of the invention can be used to treat crops in order to limit or prevent insect infestation. The present invention is especially suitable for agronomically important plants, which refers to a plant that is harvested or cultivated on a commercial scale.

Examples of such agronomic plants (or crops) are cereals, such as wheat, barley, rye, oats, rice, maize or sorghum; beet, such as sugar or fodder beet; fruit, for example pome fruit, stone fruit and soft fruit, such as apples, pears, plums, prunes, peaches, almonds, cherries or berries, for example strawberries, raspberries or blackberries; legumes, such as beans, lentils, peas or soya beans; oil crops such as oil seed rape, mustard, poppies, olives, sunflowers, coconuts, castor, cacao or peanuts; the marrow family, such as pumpkins, cucumbers or melons; fibre plants such as cotton, flax, hemp or jute; citrus fruits such as oranges, lemons, grapefruits or tangerines; vegetables such as spinach, lettuce, asparagus, cabbage species, carrots, onions, chillies, tomatoes, potatoes, or capsicums; the laurel family such as avocado, Cinnamonium or camphor; and tobacco, nuts (such as walnut), coffee, egg plants, sugar cane, tea, pepper, grapevines, hops, the banana family, latex plants and ornamentals. Also important are forage crops such as grasses and legumes.

In an embodiment plants include fibre plants, grain crops, legume crops, pulse crops, vegetables and fruit, more particularly, cotton, maize, sorghum, sunflower, lucerne, various legumes especially soybean, pigeon pea, mung bean and chickpea, tomatoes, okra and like plants.

In an embodiment plants include ornamental plants. By way of example these ornamental plants may be orchids, roses, tulips, trees, shrubs, herbs, lawns and grasses, bulbs, vines, perennials, succulents, house plants.

In an embodiment, the insect pest is a pest of an animal and the method comprises applying an extract from *Clitoria ternatea* to the animal. In an embodiment the animal may be dogs, cats, cattle, sheep, horses, goats, pigs, chicken, guinea pig, donkey, duck, bird, water buffalo, camel, reindeer, goose, Llama, alpaca, elephant, deer, rabbit, mink, chinchilla, hamster, fox, emu, ostrich.

In an embodiment the method comprises treating a habitat.

The present invention encompasses applying a *Clitoria ternatea* extract in oil, water or any carrier product to a plant affected by the pest or its surroundings, or to an animal affected by the pest. Treatment can include use of an oil-based formulation, a water-based formulation, a residual formulation, wettable powder and the like. In some embodiments, combinations of formulations can be employed to achieve the benefits of different formulation types. The extract may added to the carrier or, in the case of a liquid formulation, the carrier may have been used to extract SPCs from *Clitoria ternatea* e.g. canola oil.

In an embodiment the formulation is an oil-based formulation which may further comprise a surfactant.

In an embodiment the formulation is an oil-based formulation and the oil is a C19-C27 hydrocarbon.

In an embodiment the formulation includes a extract from *Clitoria ternatea* in a polar solvent such as an alcohol, ketone, aldehyde or sulfoxide. In particular, the formulation may be an extract from *Clitoria ternatea* in alcohol.

In an embodiment the formulation includes a methanolic extract from *Clitoria ternatea*. In an embodiment the formulation includes an ethanolic extract from *Clitoria ternatea*. In an embodiment the formulation includes an extract from *Clitoria ternatea* in low molecular weight oil such as crude and refined cotton seed oil or canola oil. Other oils include white oils, DC Tron oil (nC 21 and nC 24 oils), Canopy oil (nC27 oil), Biopest oil (nC 24 oils), dormant oil or summer oil, as known in the horticultural industry. Most of these oils are nC19-nC27 but other hydrocarbons having acceptable toxicity may be used. There are number of such products in the market which are suitable for use with the present invention. These are Sunspray oil, tea tree oil, Sunspray Ultra fine manufactured by the Sun Refining and Marketing Company.

The petroleum spray oil may be used in conjunction with suitable agronomically acceptable diluents and/or carriers and with other additives common in the art such as emulsifiers, wetting agents, surfactants, stabilizers, spreaders or the like.

In an embodiment the formulation includes an aqueous extract from *Clitoria ternatea*.

In an embodiment the formulation includes an extract from *Clitoria ternatea* in a lower hydrocarbon solvent such as hexane.

In an embodiment the formulation includes a fraction of a crude

In an embodiment the formulation includes a mixture of fractions of a crude extract from *Clitoria ternatea*.

The term "carrier" as used herein means a liquid or solid material, which can be inorganic or organic and of synthetic or natural origin, with which the active compound is mixed or formulated to facilitate application a composition according to the invention or an SPC derived from *Clitoria ternatea* is applied to a locus to be treated, or to facilitate its storage, transport and/or handling. In general, any of the materials customarily employed in formulating insecticides are suitable.

The term "locus" as used herein refers to a place to which a composition according to the invention or an SPC derived from *Clitoria ternatea* is applied. It includes application to an individual plant, a group of plants such as a plant and/or its surrounds, an animal individually or in a group and the region in which plants may be planted or in which animals may congregate, as well application directly to an insect or insects and/or the vicinity in which they are located.

The compositions of the present invention can be employed alone or in the form of mixtures with such solid and/or liquid dispersible carrier vehicles and/or other known compatible active agents such as pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The compositions of the present invention can be formulated or mixed with, if desired, conventional inert insecticide diluents or extenders of the type usable in conventional pest control agents, e.g., conventional dispersible carrier vehicles in the form of solutions, emulsions, suspensions, emulsifiable concentrates, spray powders, pastes, soluble powders, dusting agents, granules or foams.

Typical emulsifiers that may be suitable for use in the compositions of the invention, include, but are not limited to, light molecular weight oils (e.g., canola, cottonseed, groundnut, corn, germ, olive, castor, and sesame oils), and non-ionic, anionic and cationic surfactants. Blends of any of the above emulsifiers may also be used in the composition of the present invention.

Typical non-ionic surfactants include ethoxylated alkanols, in particular ethoxylated fatty alcohols and ethoxylated oxoalcohols, such as ethoxylated lauryl alcohol, ethoxylated isotridecanol, ethoxylated cetyl alcohol, ethoxylated stearyl alcohol, and esters thereof, such as acetates; ethoxylated alkylphenols, such as ethoxylated nonylphenyl, ethoxylated dodecylphenyl, ethoxylated isotridecylphenol and the esters thereof, e.g. the acetates alkylglucosides and alkyl polyglucosides, ethoxylated alkylglucosides; ethoxylated fatty amines, ethoxylated fatty acids, partial esters, such as mono-, di- and triesters of fatty acids with glycerine or sorbitan, such as glycerine monostearate, glycerine monooleate, sorbitanmonolaurate, sorbitanmonopalmitate, sorbitanmonostearate, sorbitan monooleate, sorbitantristearate, sorbitan trioleate; ethoxylated esters of fatty acids with glycerine or sorbitan, such as polyoxyethylene glycerine monostearate, polyoxyethylene sorbitanmonolaurate, sorbitanmonopalmitate, polyoxyethylene sorbitanmonostearate, polyoxyethylene sorbitan monooleate, polyoxyethylene sorbitantristearate, polyoxyethylene sorbitan trioleate; ethoxylates of vegetable oils or animal fats, such as corn oil ethoxylate, castor oil ethoxylate, tallow oil ethoxylate; ethoxylates of fatty amines, fatty amides or of fatty acid diethanolamides.

Typical anionic surfactants include salts, in particular, sodium, potassium calcium or ammonium salts of alkylsulfonates, such as lauryl sulfonate, isotridecylsulfonate, alkylsulfates, in particular fatty alcohol sulfates, such as lauryl sulfate, isotridecylsulfate, cetylsulfate, stearylsulfate-aryl- and alkylarylsulfonates, such as napthylsulfonate, dibutylnaphtylsulfonate, alkyldiphenylether sulfonates such as dodecyldiphenylether sulfonate, alkylbenzene sulfonates such as cumylsulfonate, nonylbenzenesulfonate and dodecylbenzene sulfonate; sulfonates of fatty acids and fatty acid esters; —sulfates of fatty acids and fatty acid esters; sulfates of ethoxylated alkanols, such as sulfates of ethoxylated lauryl alcohol; sulfates of alkoxylated alkylphenols; alkylphosphates and dialkylphosphates; dialkylesters of sulfosuccinic acid, such as dioctylsulfosuccinate, acylsarcosinates, fatty acids, such as stearates, acylglutamates, ligninsulfonates, low molecular weight condensates of naphthalinesulfonic acid or phenolsulfonic acid with formaldehyde and optionally urea;

Typical cationic surfactants include quaternary ammonium compounds, in particular alkyltrimethylammonium salts and dialkyldimethylammonium salts, e.g. the halides, sulfates and alkylsulfates.

In some embodiments, the insect control compositions can be combined with one or more synthetic insecticides or pesticides. In one embodiment, the insecticide or pesticide is selected from one or more of endosulfan, dicofol, chlorpyrifos, dimethoate, disulfoton, omethoate, parathion, phorate, profenofos, sulprofos, thiometon, aldicarb, carbaryl, beta-cyfluthrin, deltamethrin, esfenvalerate, fenvalerate, fluvalinate, lamda-cyhalothrin, chlorfluazuron, piperonyl butoxide, and petroleum spray oils. In another embodiment, the pesticide is a biological pesticide selected from a nuclear polyhedrosis virus and/or a plant extract known to be anti-feedant of pests. In yet another embodiment, the insecticide or pesticide is used at a reduced label rate. For example, the insecticide or pesticide may be used at half or one-third of the label rate.

The compositions of the present invention can be used to control insects by either treating a host directly, or treating an area in which the host will be located. For example, the host can be treated directly by using a spray formulation, which can be applied to a plant individually or when grouped, such as an agricultural crop.

The formulation of the present invention may further comprise other formulation auxiliaries known in the art of agrochemical formulations in customary amounts. Such auxiliaries include, but are not limited to, antifreeze agents (such as but not limited to glycerine, ethylene glycol, propylene glycol, monopropylene glycol, hexylene glycol, 1-methoxy-2-propanol, cyclohexanol), buffering agents (such as but not limited to sodium hydroxide, phosphoric acid), preserving agents (such as but not limited to derivatives of 1,2-benzisothiazolin-3-one, benzoic acid, sorbic acid, formaldehyde, a combination of methyl parahydroxybenzoate and propyl parahydroxybenzoate), stabilizing agents (such as but not limited to acids, preferably organic acids, such as dodecylbenzene sulfonic acid, acetic acid, propionic acid or butyl hydroxyl toluene, butyl hydroxyl anisole), thickening agents (such as but not limited to heteropolysaccharide and starches), and antifoaming agents (such as but not limited to those based on silicone, particularly polydimethylsiloxane). Such auxiliaries are commercially available and known in the art.

In an embodiment the present invention uses fractions, active compounds and crude extracts of *Clitoria ternatea* formulated in oil and emulsifiers to control cotton pests.

Preferably, the *Clitoria ternatea* extracts and formulations are suitable for killing the insect. The extract or formulation in water when applied to the plant or insect penetrates the insect's cuticle layers or is ingested to kill the insects or the residue of the extract on the plant can repel insects or deter the insects from egg laying or feeding. The formulation can kill or deter insect egg laying or feeding within 3-4 days of application to the insect or the target crop.

In an embodiment the *Clitoria ternatea* extract, fractions, crude or active compounds in oil is dissolved in water and applied to the crops infested with the target insects. The rate of application of the composition of the invention is typically between 1-2 liters of oil formulated extracts or active compounds dissolved in 1-500 liters of water, preferably 60-100 liters of water per hectare. In an embodiment, the rate of application is about 2 liters of oil formulated extracts dissolved in about 100 liters of water per hectare of plants. In an alternative embodiment, the rate of application is about 2 liters of oil formulation. Typically the treatment may involve at least four sprays at 14-28 day intervals.

Alternatively, the method may comprise applying 1-3000 ml, preferably 1000-2000 ml, of oil formulated extracts or active compounds per hectare of plants in the absence of dissolution of the oil formulated extracts or active compounds in water, particularly when smaller areas are to be treated. When, for example, plants in a greenhouse, are to be treated.

While not wishing to be bound by theory, it is believed that the present invention controls moths and their larvae and chewing or sap sucking pests by repelling the pests, suppression of egg laying, deterrence of feeding and direct contact activity of the plant extract which kills the insect. There may also be method of control of other non-target pests and conservation of natural enemies of the moths and their larvae and chewing or sap sucking pests through treatment of the habitat.

In an embodiment the *Clitoria ternatea* structure used is the leaves, stems, roots, pods, seeds and a combination of any of the plant parts. These may be used as fractions or crude extracts in formulations such as low and high molecular oil or water or any other carriers to control moths and their larvae and chewing or sap sucking pests through repellent action, suppression of egg laying, deterrence of feeding and direct contact activity.

Botanically, *Clitoria ternatea* belongs to the family Fabaceae and sub family Papilionaceae. The family Fabaceae is a large family of around 12,000 species that cover a wide range of life forms from annuals to rainforest trees. Widespread in tropical and temperate regions, and the source of many economically important food plants, fodder crops, ornamentals, timber species and weeds, *Clitoria ternatea* is a climbing perennial, with sparsely hairy leaves usually with five leaflets. The flowers are large, to 5 cm, solitary or in pairs, blue with a yellow blotch in the centre, produced between April and June. In Australia it is a garden escape pest which has naturalised on creek banks and around waterholes throughout the Kimberley; also around coastal settlements in the Pilbara and Gascoyne. It is also used as a forage crop in large part of north QLD. It is pantropical, and probably native to tropical America.

For purposes of simplicity, the term "insect" or its equivalents or derivatives such as "insecticidal" shall be used in this application; however, it should be understood that the term "insect" refers, not only to insects but to their immature forms and larvae.

Those skilled in the art will recognize that not all compounds are equally effective against all insects. In embodiments the compositions display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Larvae of the order Lepidoptera include, but are not limited to, armyworms, cutworms, loopers, and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (Xylomyges) *curialis* Grote (citrus cutworm); borers, casebearers, webworms, coneworms, and skeleton izers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grysella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenee (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rósslerstamm (summer fruit *tortrix* moth); *Cochylis hospes* Walsingham (banded sunflower moth); *Cydia latiferreana* Walsingham (filberworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubηcola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guerin-Meneville (Chinese Oak Tussah Moth); *Bombyx mori* Linnaeus (Silkworm); *Bucculatηx thurbeηella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guerin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp. Of interest are larvae and adults of the order Coleoptera including weevils from the families Anthribidae, Bruchidae, and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles, and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith & Lawrence (northern corn rootworm]; *D. undecimpunctata howardi* Barber (southern corn rootworm); *Chaetocnema pulicaria* Melsheimer (corn flea beetle); *Phyllotreta cruciferae* Goeze (corn flea beetle); *Colaspis brunnea* Fabricius (grape colaspis); *Oulema melanopus* Linnaeus (cereal leaf beetle); *Zygogramma exclamationis* Fabricius (sunflower beetle)); beetles from the family Coccinellidae (including, but not limited to: *Epilachna varηvestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elatehdae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebhonidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gehin (wheat midge); *Neolasioptera murtfeldtiana* Felt, (sunflower seed midge)); fruit flies (Tephritidae), *Oscinella frit* Linnaeus (frit flies); maggots (including, but not limited to: *Delia platura* Meigen (seedcorn maggot); *D. coarctata* Fallen (wheat bulb fly); and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciands, and other Nematocera. Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, lssidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae, Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae, and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/

Mordvilko (Russian wheat aphid); *Dysaphis plantaginea* Paaserini (rosy apple aphid); *Eηosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid); and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stal (rice leafhopper); *Nilaparvata lugens* Stal (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyη* Ash mead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schaffer (cotton stainer); *Euschistus servus* Say (brown stink bug); *E. vaηolaηus* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments of the present invention may be effective against Hemiptera such, *Calocoris norvegicus* Gmelin (strawberry bug); *Orthops campestris* Linnaeus; *Plesioconηs rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; Coreidae spp.; Pyrrhocoridae spp.; Tinidae spp.; Blostomatidae spp.; Reduviidae spp.; and Cimicidae spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Ehophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); /. *holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae. Insect pests of the order Thysanura are of interest, such as *Lepisma saccharina* Linnaeus (silverfish); *Thermobia domestica* Packard (firebrat).

In an embodiment the insects are selected from cotton bollworm, native budworm, green mirids, aphids, green vegetable bugs, apple dimpling bugs, *thrips* (plaque *thrips*, tobacco *thrips*, onion *thrips*, western flower *thrips*), white flies and two spotted mites. In an embodiment the insect pests of animals include fleas, lice, mosquitoes, flies, tsetse flies, ants, ticks, mites, silverfish and chiggers.

Insect pests may be tested for insecticidal activity of compositions of the embodiments in early developmental stages, e.g., as larvae or other immature forms. The insects may be reared in total darkness at from about 20° C. to about 30° C. and from about 30% to about 70% relative humidity. Methods of rearing insect larvae and performing bioassays are well known to one of ordinary skill in the art.

In some embodiments, the insecticidal effect is an effect wherein treatment with a composition causes at least about 10% of the exposed insects to die. In some embodiments, the insecticidal effect is an effect wherein treatment with a composition causes at least about 25% of the insects to die. In some embodiments the insecticidal effect is an effect wherein treatment with a composition causes at least about 50% of the exposed insects to die. In some embodiments the insecticidal effect is an effect wherein treatment with a composition causes at least about 75% of the exposed insects to die. In some embodiments the insecticidal effect is an effect wherein treatment with a composition causes at least about 90% of the exposed insects to die.

Beneficial insects that can be conserved by the present invention include (1) predatory beetles (see table 11) *Harmonia arcuata* (Fabricius) adults, *Diomus notescens* (Blackburn) adults, *Coccinella repanda* (Thunberg) adults, *Dicranolauis bellulus* (Guerin); (2) predatory bugs such as *Geocoris lubra* (kirkaldy adults, *Cermatulus nasalis* (Westwood) adults, *Nabis capsiformis* (Germar), (3) Spiders especially salticidae, *Araneus* spp. *Oxypes* spp. and (Parasitoids) *Pterocormus promissorius* (Erichson), *Heteropelma scaposum* (Morley), *Netelia producta* (Brulle).

Embodiments of the invention are also directed to making an improved insect control agent by identifying one or more fractions in a complex agent, screening the one or more fractions using the methods disclosed herein, and characterizing the one or more fractions as having a positive or negative effect on potential activity against a target insect.

In some embodiments, one or more fractions in a complex agent (such as, for example, an essential oil) can be isolated using fractionation techniques including, for example, differential solvent extraction, fractional distillation, fractional crystallization, fractional freezing, dry fractionation, detergent fractionation, solvent extraction, supercritical $CO_2$ fractionation, vacuum distillation, column chromatography, reverse-phase chromatography, high-pressure liquid chromatography, and the like. These methods are known to those of skill in the art.

Vacuum distillation is preferred, because it is relatively simple to employ and does not require the use of solvents.

In some embodiments, one or more fractions of a complex agent can be isolated by column chromatography using silica or alumina solid support. An organic solvent, including for example, alkanes such as hexanes and petroleum ether, toluene, methylene chloride (or other halogenated hydrocarbons), diethyl ether, ethyl acetate, acetone, alcohol, acetic acid, and the like, can be used alone or in combination as the column solvent, or mobile phase. In some embodiments, the complex agent is fractionated by column chromatography using an increasing concentration of a polar solvent as eluting solvent. Methods of column chromatography and solvents common for its use are well known in the art.

In some embodiments, SPCs can be isolated by solvent extraction. For example, an essential oil can be combined with an organic solvent, including, for example an organic solvent such as methanol, acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxyethane (glyme, DME), dimethylether, dimethyl-formamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methyl t-butyl ether (MTBE), methylene chloride, JV-methyl-2-pyrrolidinone (NMP), nitromethane, pentane, petroleum ether (ligroine), 1-propanol, 2-propanol, pyridine, tetrahydrofuran (THF), toluene, triethyl amine, water, heavy water, o-xylene, m-xylene, and/or -xylene. Other organic solvents known to those of skill in the art can also be employed. The mixture of the SPC and the organic solvent can then be combined with an extraction solvent that is not miscible in the organic solvent, including, for example, water, ethanol, and methanol. This combination is shaken vigorously in a glass container such as a separatory funnel for several minutes, then allowed to settle into separate phases for several minutes. The lower, denser phase is then allowed to drain from the separatory funnel. The organic phase can then be repeatedly re-extracted with the extraction solvent to further partition compounds that are soluble in the extraction solvent from the organic phase. The volume of the organic phase and the extracted phase can then be reduced in volume using rotary evaporation, yielding two separate fractions of the SPC.

In some embodiments, a method for identifying an improved agent against a target insect can include the identification of the compounds present in either a complex agent or individual isolated fractions of a complex agent and screening of the ingredient compounds for their activity. Identification of the compounds can be performed by analyzing the complex agent or an isolated fraction thereof by High-Performance Liquid Chromatography (HPLC) or gas chromatography (GC) coupled with Mass Spectrometry (MS). Ingredient compounds can also be identified by first enriching or purifying individual ingredients to homogeneity using techniques including, for example, differential solvent extraction, fractional distillation, vacuum distillation, fractional crystallization, fractional freezing, dry fractionation, detergent fractionation, solvent extraction, supercritical CO2 fractionation, column chromatography, reverse-phase chromatography, high-pressure liquid chromatography, and the like. Enriched or purified components can be identified using spectroscopy techniques, including, for example, infrared (IR) spectroscopy, Raman spectroscopy, nuclear magnetic resonance spectroscopy (NMR), and the like.

Some embodiments relate to the use of chemical derivatives or analogs of chemicals identified to generate an improved agent against a target insect. Chemical derivatives of the chemicals identified can include compounds derivatised with an inorganic or organic functional group. In some embodiments, the chemical derivative is a compound derivatised with an organic functional group. In some embodiments, the organic functional group can be an alkyl group. In some embodiments, the organic functional group can be a methyl, ethyl, propyl, butyl, ceryl, decyl, heptyl, hexyl, myricyl, myristyl, nonyl, octyl, palmityl, pentyl, stearyl, isopropyl, isobutyl, lignoceryl, pentacosyl, heptacosyl, montanyl, nonacosyl, pentan-2-yl, isopentyl, 3-methylbutan-2-yl, tert-pentyl, neopentyl, undecyl, tridecyl, pentadecyl, margaryl, nonadecyl, arachidyl, henicosyl, behenyl, tricosyl, cyclobutyl, cyclopropyl group, or the like. In some embodiments, the organic functional group can be an aryl group. In some embodiments, the organic functional group can be a phenyl or biphenyl-4-yl group.

In some embodiments, the improved agent against a target insect includes a chemical derivative that is a halogenated derivative of a compound identified. In some embodiments, the chemical derivative is a fluorinated, chlorinated, brominated, or iodinated derivative.

In some embodiments, the improved agent against a target insect includes a chemical derivative that is an alkenylated derivative of a compound. In some embodiments, the chemical derivative is an oleylated, allylated, isopropenylated, vinylated, prenylated, or phytylated derivative.

In some embodiments, the improved agent against a target insect includes a chemical derivative that is a hydroxylated derivative of a compound identified.

In some embodiments, the improved agent against a target insect includes a chemical derivative that is a thiolated derivative of a compound identified.

In some embodiments, the improved agent against a target insect includes a chemical derivative that is a carboxylated derivative of a compound identified.

In some embodiments, the improved agent against a target insect includes a chemical derivative that is an amidated derivative of a compound identified.

In some embodiments, the improved agent against a target insect includes a chemical derivative that is an esterified derivative of a compound identified.

In some embodiments, the improved agent against a target insect includes a chemical derivative that is acylated derivative of a compound identified.

In some embodiments, the improved agent against a target insect includes a chemical derivative that is a sulfonated derivative of a compound identified.

In some embodiments, the improved agent against a target insect includes a chemical derivative that is derivatised by introducing a homologue of a substituent group.

In some embodiments, the improved agent against a target insect includes a chemical derivative that is derivatised by moving a substituent around a ring to a different position.

In some embodiments of the invention, the efficacy of a test composition can be determined by conducting studies with insects. For example, the efficacy of a test composition for killing an insect, altering its propensity to feed or lay eggs, or the like, an insect can be studied using controlled experiments wherein insects are exposed to the test composition. In some embodiments, the toxicity of a test composition against an insect can be studied using controlled experiments wherein insects are exposed to the test composition.

In some embodiments, the formulations consist of an emulsifier of high solvency and the capacity to form stable emulsions of the total formulation in water and a "carrier" oil which may also have pesticidal properties. A preferred "carrier" oil is an esterified vegetable oil.

MODES OF CARRYING OUT THE INVENTION

A study was conducted to identify plants that could be used as a trap or refuge crop within a commercial cotton system to control cotton pests. In this study, a wide range of plants such as lucerne, pigeon pea, sorghum, sweet corn and *Clitoria ternatea* and cotton genotypes were planted in 12 meter row strips within commercial cotton fields. Pest succession on these crops especially *Helicoverpa* spp. eggs and larval counts were carried out fortnightly throughout the cotton season. The results of the trial revealed that *Helicoverpa* spp. and other cotton pest infestation on *Clitoria ternatea* was significantly lower than that on cotton and other refuge crops. Thus the plant was thought to be containing some SPCs that may either kill or modify the behaviour of insect pests. Since *Clitoria ternatea* had not received previous attention in terms of identification of SPCs and use of these SPCs to control pests, it was anticipated that a bioassay-directed fractionalisation of the plant may reveal compounds or fractions for biological pest control previously unknown.

EXAMPLE 1

*Clitoria ternatea*: Toxicity Feeding Experiments

Based on the results of the field trial that revealed that *Helicoverpa* spp. and other cotton pest infestation of *Clitoria ternatea* was significantly lower than that on cotton and other refuge crops tested, an investigation of possible reasons for this and the SPCs involved was undertaken. The study also determined the location in the plant structures that may contain the toxic compounds and the use of *Clitoria ternatea* as a formulated product to manage pests on agricultural crops.

Toxicity of Plant Structures to *Helicoverpa* Spp. $1^{st}$ and $2^{nd}$ Instar Larvae

*Clitoria ternatea* structures or parts (viz; new, middle, old leaves; whole and cut pods; green (immature), mature seeds; crushed immature seeds and crushed mature seeds) were prepared and placed individually on a filter paper moistened with 100 μL of distilled water in a petri dish 12 mm in diameter. One second instar larva of *Helicoverpa* spp. was placed on each plant structure in each petri dish and sealed. Each treatment was replicated four times. The dishes were then placed into a Labec incubator running at 25° C. (±2° C.) with 14 hours light/10 hours dark and checked daily for mortalities for up to 9 days. Percent mortalities for each treatment were calculated at days 1-2, 3-4 and 5-9 days.

Analysis of Data

All experimental data were analysed using the ANOVA procedures of Instat, version 2.03 (Graphpad Instat Software Inc., San Diego, Calif., USA). Tukey-Kramer multiple comparison tests were used to separate the means.

Results

Table 1 presents the mortality of *Helicoverpa* spp on different parts of *Clitoria ternatea* (*Clitoria ternatea*). The results show that the toxin(s) in *Clitoria ternatea* are located in all plant parts with the highest in the leaves. *H. punctigera* was found to be more susceptible to the toxin(s) in *Clitoria ternatea* than *H. armigera* larvae.

TABLE 1

Mortality of second instar larvae of *Helicoverpa* spp. on different structures of *Clitoria ternatea*

| Species | Plant Structure | Part | Percent Mortality | | | |
|---|---|---|---|---|---|---|
| | | | Day 1-2 | Day 3-4 | Day 5-9 | Total |
| *H. armigera* | Leaf | New | 20.0 | 10.0 | 20.0 | 50.0 |
| | | Middle | 10.0 | 30.0 | 0 | 40.0 |
| | | Old | 20.0 | 30.0 | 31.1 | 81.1 |
| | Whole seed | Green | 31.1 | 0 | 20.0 | 51.1 |
| | | Mature | 63.3 | — | — | 63.3 |
| | Crushed seed | Green | 20.0 | 11.1 | 40.0 | 71.1 |
| | | Mature | 0 | 41.1 | 20.0 | 61.1 |
| *H. punctigera* | Leaf | New | 88.9 | — | — | 88.9 |
| | | Middle | 77.8 | — | — | 77.8 |
| | | Old | 88.9 | — | — | 88.9 |
| | Whole seed | Green | 12.5 | 0 | 10.0 | 22.5 |
| | | Mature | 50.0 | — | — | 50.0 |
| | Crushed seed | Green | 44.4 | 0 | 10.0 | 54.4 |
| | | Mature | 11.1 | 62.5 | — | 73.6 |

[1]Control treatment: Newly opened cotton leaf as compared to *Clitoria ternatea*'s leaf; Cotton square and boll as compared to *Clitoria ternatea*'s pod and cotton seed as compared to *Clitoria ternatea*'s seed. Larval mortality on cotton (control mortality) was used for calculation of corrected mortality.

EXAMPLE 2

Crude Extraction of *Clitoria ternatea*

Choice of Solvent and Extraction Procedure

Three solvents with different polarity used for extraction were water (high polarity), methanol (intermediate polarity) and hexane (apolar). Both surface rinsing and homogenisation were employed in the early stages of the study. The washing process involved shaking the leaves in solvent for 30 seconds and evaporating the solvent to a volume that achieved a concentration equivalent to 1 g fresh leaf weight per mL. Homogenates were prepared by submerging leaves in solvent overnight before blending in an industrial Waring blender for 10 minutes. The blended leaf material was then filtered and evaporated to the same adjusted volume as for the surface wash. In the case of hexane extraction, any aqueous phase was eliminated using a separating funnel and the hexane evaporated to the appropriate volume.

Methanol and hexane extracts were concentrated using a rotary evaporator and water extracts with a freeze drier.

Methanol Extract

For the preparation of methanolic extracts for SPE fractionation and later supply of fractions for bioassay, freeze-dried plant material was used. Up to twelve containers, each containing up to ca. 45 g plant material, were dried to constant weight (24-30 hours). Freeze-dried weight was generally 25%-30% of the wet weight.

Freeze-dried material (weight) was chopped into 2-3 mm portions and weighed into a 150 mL beaker. HPLC-grade methanol, 50 mL, was added and the sample ultrasonicated for 20 minutes. The solvent was filtered and the plant mass treated a further three times in the same way, with filtrates being combined, then evaporated to dryness using a rotary-evaporator. Water-bath temperature was maintained at 40° C.

Ethanol Extract

An exhaustive extraction was made on 500 g of air-dried, ground plant material using hot ethanol. The Soxhlet extractor was run for 24 hours and on evaporation of the solvent yielded 80 g of extract (16%). For comparison another extraction was performed on another sample using ethanol at ambient temperature and steeping over 24 hr. This process yielded 25 g of extract (5%) on the first steeping. No repeated extracts were made.

Fractionation of Extracts

Solid phase extraction (SPE) was used to fractionate extracts and to provide fractions for biological assays against insects using C18 hydrophobic silica-based solid phase SPE cartridges comprising a 40 μm/120 μm irregularly-shaped acid-washed silica, (60 Å mean porosity) with a trifunctional octadecyl bonded functional group (Varian Bond Elute (Part No. 12256001) or Phenomenex Strata C18-E (Part No. 8B-S001-JCH)). All cartridges were processed simultaneously on an Alltech Vacuum manifold (Part No. 210351)). The SPE cartridges were used to accommodate 1.5 g wet-weight of freeze-dried plant material and gave a better band definition when dried extracts were dispersed on Celite filter aid (Merck Celite 545, 0.02-0.1 mm) before being added to a conditioned cartridge as a solid. To this end, the bulb end of a Pasteur pipette was used to deliver a volume, measured to the constriction in the pipette neck (ca. 0.2 g), of Celite, 6 times to the remaining 9 mL of sample, which had been transferred, with rinsing, to a small pre-weighed vial which was attached to the rotary evaporator. After thorough mixing of the Celite, the vial contents were dried to a paste under $N_2$, then to completeness using the rotary evaporator. The SPE cartridges were conditioned by passing through 5 mL of methanol followed by almost all of 5 mL of water. One-sixth of the dried sample/Celite residue was transferred by spatula to each of six conditioned SPE cartridges. The general procedure then involved passing 5 mL water through the column followed by aliquots of methanol/water mixtures, pure methanol, then acetone, with all eluates being collected.

HPLC Analysis

An Agilent 1100 instrument with diode array detector was used for the analytical-scale chromatography. The column was a silica based Phenomenex Luna 5 μm C18 (2), 150 mm×4.6 mm, maintained at 30° C. Varying volumes, but normally 20 μL, of filtered sample were analysed via an acidified methanol/water gradient elution program from 5% MeOH to 100% MeOH in 20 minutes, held to 28 minutes and returned to 5% MeOH by 30 minutes and held to 37 minutes to equilibrate. Both components of the mobile phase contain 0.5% acetic acid. Flow rate was usually 1 mL/min. The photo diode-array detector collected data at 254 nm, 280 nm, 360 nm, 430 nm and 450 nm. All chromatograms illustrated below were those acquired at 280 nm.

Results

The chemical and structural analyses of SPE fractions from a methanolic extract of *Clitoria ternatea* are given in FIG. 1. The uppermost trace is that of the crude methanol extract of the freeze-dried plant material. Those below represent the various fractions (1-6) sequentially eluted from an SPE cartridge as solvent polarity is increased. As expected, the reversed-phase separation process common to both the SPE fractionation and the HPLC analysis results in chemical components with greater affinity for the stationary phase appearing at longer retention times in later fractions.

EXAMPLE 3

Efficacy of *Clitoria ternatea* Fractions on Oviposition of *Helicoverpa* Spp. on Cotton Plants in the Mesh House (No-Choice Test)

The experiment was conducted to determine oviposition deterrent activities of fractions isolated from *Clitoria ternatea*. The *Clitoria ternatea* fractions tested were (1) Fraction 1, (2) Fraction 2, (3) Fraction 3, (4) Fraction 4, (5) Fraction 5 and (6) Fraction 6, and (7) Untreated (control). Each treatment was replicated 4 times in a complete randomised design. Plants used in the experiment were grown in 8 cm diameter pots in black soil (from the field) and watered three times a week. The plants were fertilised once. Potted plants were kept and maintained in the mesh house which allowed a greater degree of exposure to the natural environment but protected them from potential pest infestation. Once the plants had reached the 4-true-leaf stage, 0.25 mL of extract of each treatment was placed on each leaf (1 mL in one pot) and spread evenly over the surface. The plants were then covered and three mated (5 day post emergence) female moths were released into the cages. Eggs were counted three days after treatment. The Oviposition Deterrent Index (ODI) was calculated as follows: ODI=100× (C−T)/(C+T) where C=total eggs laid in control; T=total eggs in treated filter paper.

Analysis of Data

All experimental data were analysed using the ANOVA procedures of Instat, version 2.03 (Graphpad Instat Software Inc., San Diego, Calif., USA). Tukey-Kramer multiple comparison tests were used to separate the means Results No choice tests conducted under laboratory conditions using *H. armigera* adult females confirmed that *Clitoria ternatea* fraction 3 and fraction 4 (Table 2) had significantly lower (P<0.001) number of eggs per plant laid on them than all the other fractions tested (Table 2). Thus the two fractions may contain oviposition deterring compounds.

TABLE 2

No-choice oviposition test of *Helicoverpa armigera* females on filter papers treated with *Clitoria ternatea* fractions 1-3

| Treatments | No. eggs/plant ± SE | [1]Oviposition Deterrent Index (ODI) |
|---|---|---|
| Fraction 1 | 32.75 ± 25.39 a | 20.1 a |
| Fraction 2 | 41.00 ± 14.41 a | 9.1 a |
| Fraction 3 | 17.50 ± 7.84 b | 47.6 b |
| Fraction 4 | 6.50 ± 1.19 a | 42.2 a |
| Fraction 5 | 58.25 ± 22.96 b | −56.9 b |
| Fraction 6 | 35.00 ± 10.40 b | −37.3 b |
| Control (water) | 49.25 ± 17.21 a | 0.0 a |

Means within columns followed by the same letter are not significantly different (P > 0.05) (Tukey-Kramer Multiple comparison test).
[1]Oviposition Deterrent Index (ODI) was calculated as follows: ODI = 100 × (C − T)/(C + T); where C = Total eggs laid in control; T = total eggs in treated filter paper.

EXAMPLE 4

Efficacy of *Clitoria ternatea* Fractions on the Feeding of *Helicoverpa* Spp. $2^{nd}$ Instar Larvae on Leaf Discs of Cotton Plants in the Laboratory (No-Choice Test)

The experiment was conducted using cotton leaves in a no-choice test. *H. armigera* $2^{nd}$ instar larvae were used for the feeding bioassays. The *Clitoria ternatea* fractions tested were (1) Fraction 1, (2) Fraction 2, (3) Fraction 3, (4) Fraction 4, (5) Fraction 5, (6) Fraction 6, and (7) Water-treated (control). Each treatment was replicated 4 times in a complete randomised design. Three day-old cotton leaves taken from plants grown in the glasshouse were used for the study. The leaves were treated with 1 mL of extract of each treatment. To prevent preference for or avoidance of the extract, 0.5 mL was applied to each side of the leaf surface. The leaves were allowed to air dry in the fume hood for 1 hour.

Once air dried, a 25 mm disc of each treated leaf was cut out, weighed and placed in a 55 mm petri dish. The filter paper was moistened with 100 µL of distilled water to prevent the disc from drying out. One larva of the desired size was weighed and placed into each dish. The dishes were then placed into a Labec incubator running at 25° C. (±2° C.) with 14 hours light/10 hours dark for 48 hours.

Forty-eight hours after treatment, both the leaf discs and the larvae were then weighed. The differences in weights of both the leaf discs and larvae before and after the experiments were calculated for each treatment and control to determine any antifeedant effect of the treatments.

Analysis of Data

Figure 2:
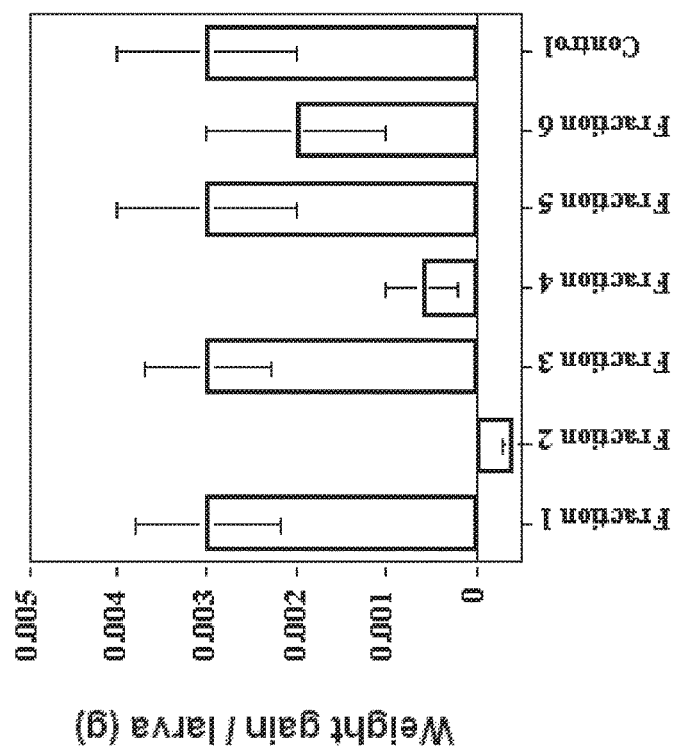
FIG. 2 graphically illustrates the feeding response of *Helicoverpa armigera* $3^{rd}$ instar larvae on cotton leaves treated with *Clitoria ternatea* fractions (no-choice tests)
Figure 2:
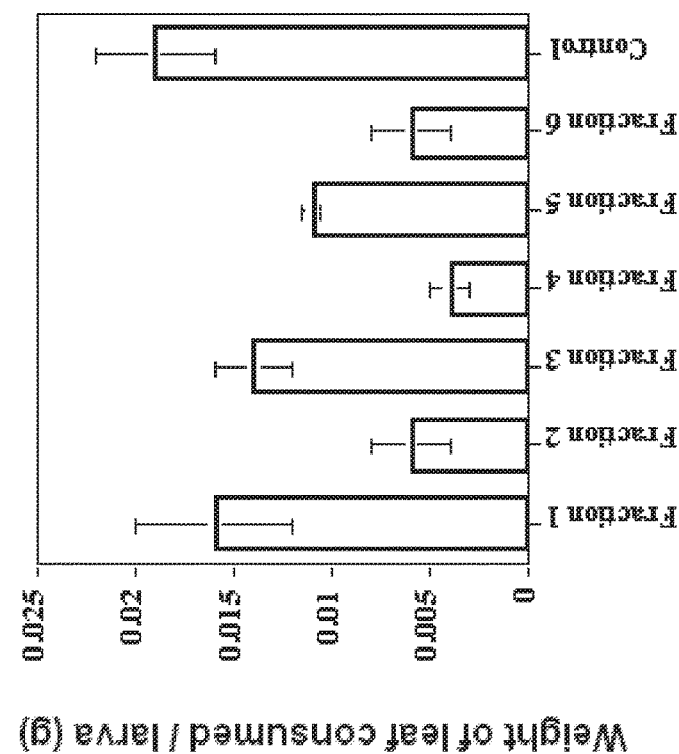

All experimental data were analysed using the ANOVA procedures of Instat, version 2.03 (Graphpad Instat Software Inc., San Diego, Calif., USA). Tukey-Kramer multiple comparison tests were used to separate the means Results In no-choice bioassays conducted using the fractions of *Clitoria ternatea* and *H. armigera* $2^{nd}$ and $3^{rd}$ instar larvae, leaves treated with fractions 2, 4 and 6 were consumed at lower levels and resulted in lower weight gains by the larvae compared to the other fractions and the control tested (FIG. 2a). Fraction 2 appears to have a stronger deterrent effect than fraction 4 and 6 so much so that the $2^{nd}$ instar resulted in a weight loss (FIG. 2b).

EXAMPLE 5

Efficacy of *Clitoria ternatea* Fractions on Toxicity of *Helicoverpa* Spp. $2^{nd}$ Instar Larvae in the Laboratory (No-Choice Test)

The experiment was using cotton leaves in a no-choice test. *H. armigera* $2^{nd}$ instar larvae were used for the feeding bioassays. The *Clitoria ternatea* fractions tested were (1) Fraction 1, (2) Fraction 2, (3) Fraction 3, (4) Fraction 4, (5) Fraction 5, (6) Fraction 6, and (7) Water-treated (control). Each treatment was replicated 4 times in a complete randomised design. Three day-old cotton leaves taken from plants grown in the glasshouse were used for the study. The leaves were treated with 1 mL of extract of each treatment. To prevent preference for or avoidance of the extract, 0.5 mL was applied to each side of the leaf surface. The leaves were allowed to air dry in the fume hood for 1 hour.

Once air dried, one $2^{nd}$ instar larva was placed in a petri dish with a leaf disc 25 mm in diameter, on a filter paper moistened with 100 µl of distilled water and sealed. The dishes were then placed into a Labec incubator running @ 25° C. (±2° C.) with 14 hours light/10 hours dark and checked daily for larval mortalities for 3 days.

Analysis of Data

All experimental data were analysed using the ANOVA procedures of Instat, version 2.03 (Graphpad Instat Software Inc., San Diego, Calif., USA). Tukey-Kramer multiple comparison tests were used to separate the means.

Results

Figure 3:
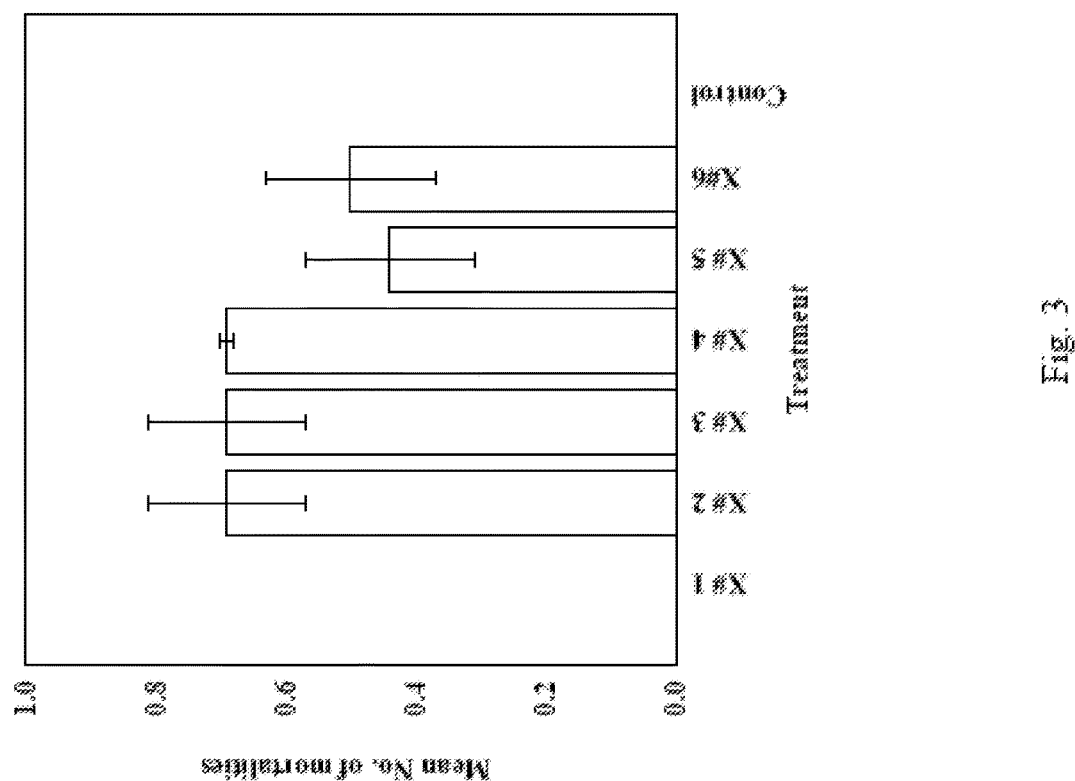
FIG. 3 graphically illustrates the antibiotic effects of *Clitoria ternatea* fractions on $2^{nd}$ instar *H. armigera* resulting in mortalities after 48 hours.

The results of the study also showed that the *Clitoria ternatea* fractions had antibiotic effects on 2nd instar *H. armigera* larvae. The experiments showed that fractions 2, 3 and 4 contain compounds toxic to the larvae due to the higher mortality rates in these treatments after 48 hours than the control (FIG. 3). This figure indicates that after 48 hours 7 of the 10 larvae tested were dead within 48 hour period.

EXAMPLE 6

Feeding Deterrent Activity of *Clitoria ternatea* Fraction 2 Applied to Leaves of Susceptible Cotton Genotype (Lumein)

Masking experiments were conducted to observe and quantify the feeding response effects or antifeedant effects of *Helicoverpa* spp. 2nd instar larvae towards a cotton genotype known to stimulate *Helicoverpa* spp. larval feeding. Tests were conducted in the laboratory at ACRI using *H. armigera* 2nd instar larvae to determine the effects of the interactions of using a combination of an identified feeding stimulant (Lu Mein fraction 3) and a feeding deterrent (*Clitoria ternatea* fraction 2).

In this experiment, *Clitoria ternatea* fraction 2 was applied to leaf discs of a cotton genotype called Lu Mein. A second leaf disc was treated with water. Once air dried, one 2nd instar larva was placed in a petri dish with a leaf disc 25 mm in diameter, on a filter paper moistened with 100 µL of distilled water and sealed. The experiment was replicated 10 times in a randomised complete block design. The dishes were then placed into a Labec incubator running at 25° C. (±2° C.) with 14 hours light/10 hours dark. The larvae were left to feed for 48 hours and the weight of leaf consumed and larval weight were calculated and analysed for differences in leaf consumed and weight loss or gain between the *Clitoria ternatea* fraction 2-treated and water-treated leaf discs.

Analysis of Data

All experimental data were analysed using the ANOVA procedures of Instat, version 2.03 (Graphpad Instat Software Inc., San Diego, Calif., USA). Tukey-Kramer multiple comparison tests were used to separate the means.

Results

Figure 4:
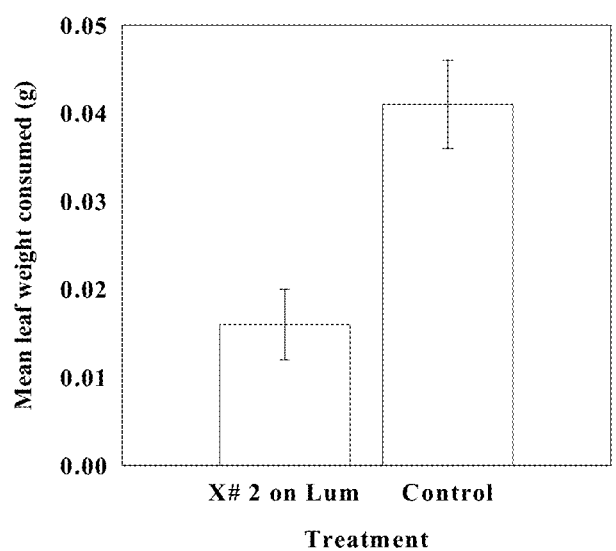
FIG. 4 shows the no-choice feeding response of 2nd instar *H. armigera* to the masking effects of *Clitoria ternatea* F2 on Lu Mein leaves (feeding attractant) on leaf weight consumed.
Figure 5:
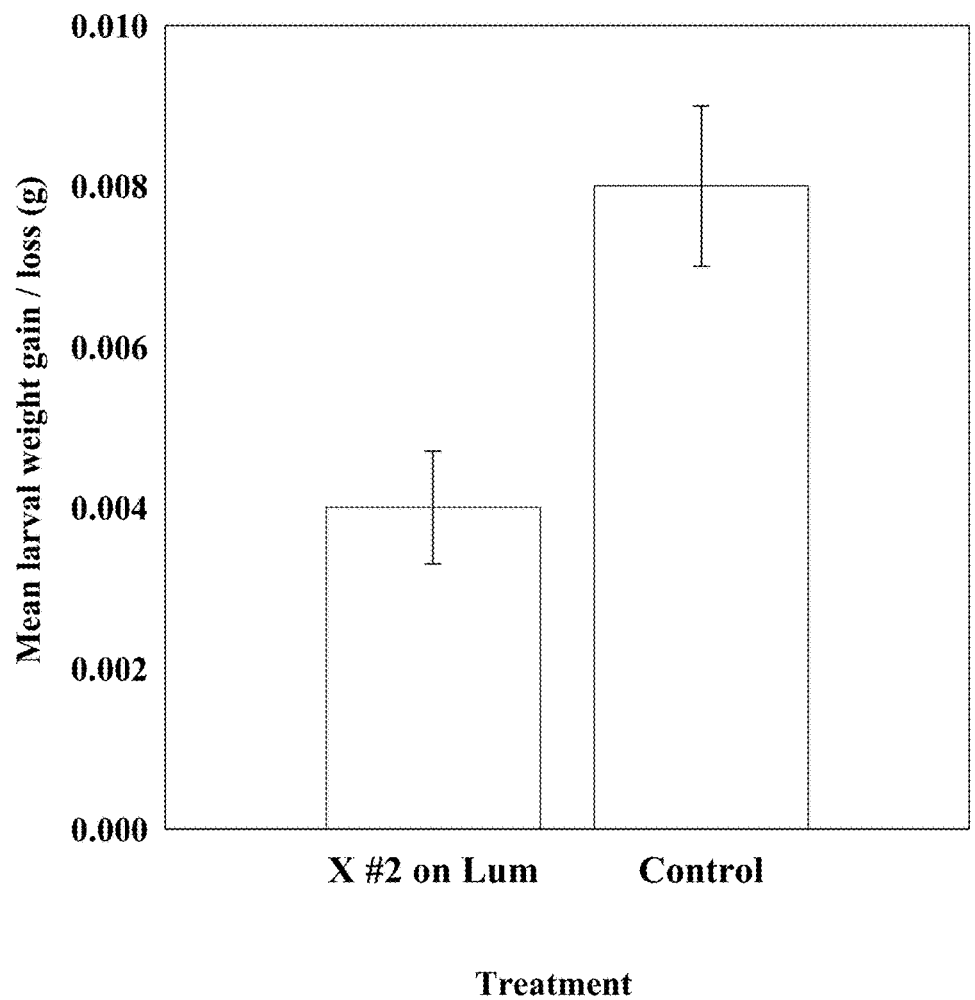
FIG. 5 shows the no-choice masking effect of *Clitoria ternatea* fraction #2 on Lu Mein Leaves on larval weight of $2^{nd}$ instar *H. armigera* (summary of 3 experiments)

The results of the study showed that *Clitoria ternatea* fraction 2 masked the feeding stimulant effect of the Lu Mein leaves reducing the quantity of leaf consumed per larvae compared to the water-treated (FIG. 4). This resulted in a lower larval weight gain compared to the control (FIG. 5).

EXAMPLE 7

Effect of *Clitoria ternatea* Fractions Formulated in Hexane on Oviposition of *Helicoverpa* Spp. on Cotton Plants

*Clitoria ternatea* fractions 2, 3 and 4 were combined and formulated in hexane for studies to determine the oviposition of *Helicoverpa* spp. in the mesh house. Three experiments were conducted in a mesh cage (100 cm×50 cm×70 cm) when the plants were at a 6 true leaf stage. Four treatments representing concentrations of 0 (control), 20% v/v, 15% v/v and 10% v/v of the *Clitoria ternatea* formulations were used. Ten cotton plants were randomly allocated to each treatment and enclosed in the mesh cage. Each treatment was applied to run-off using a small hand-held sprayer. The control plants were sprayed with water. Each treatment was replicated 4 times in different cages in a complete randomised design. Twenty mated female moths were released into each cage to lay on the treated plants. At three days after treatment, the number of eggs per plant in each treatment was counted and the number of eggs per plant calculated. Data was expressed as number of eggs per plant per treatment.

Analysis of Data

All experimental data were analysed using repeated measures ANOVA (Graphpad Instat Software, Inc., v2.03, San Diego, Calif., USA). Treatment and sample dates were the independent variables. Tukey-Kramer Multiple Comparisons test was used to separate the means.

Results

Figure 6:
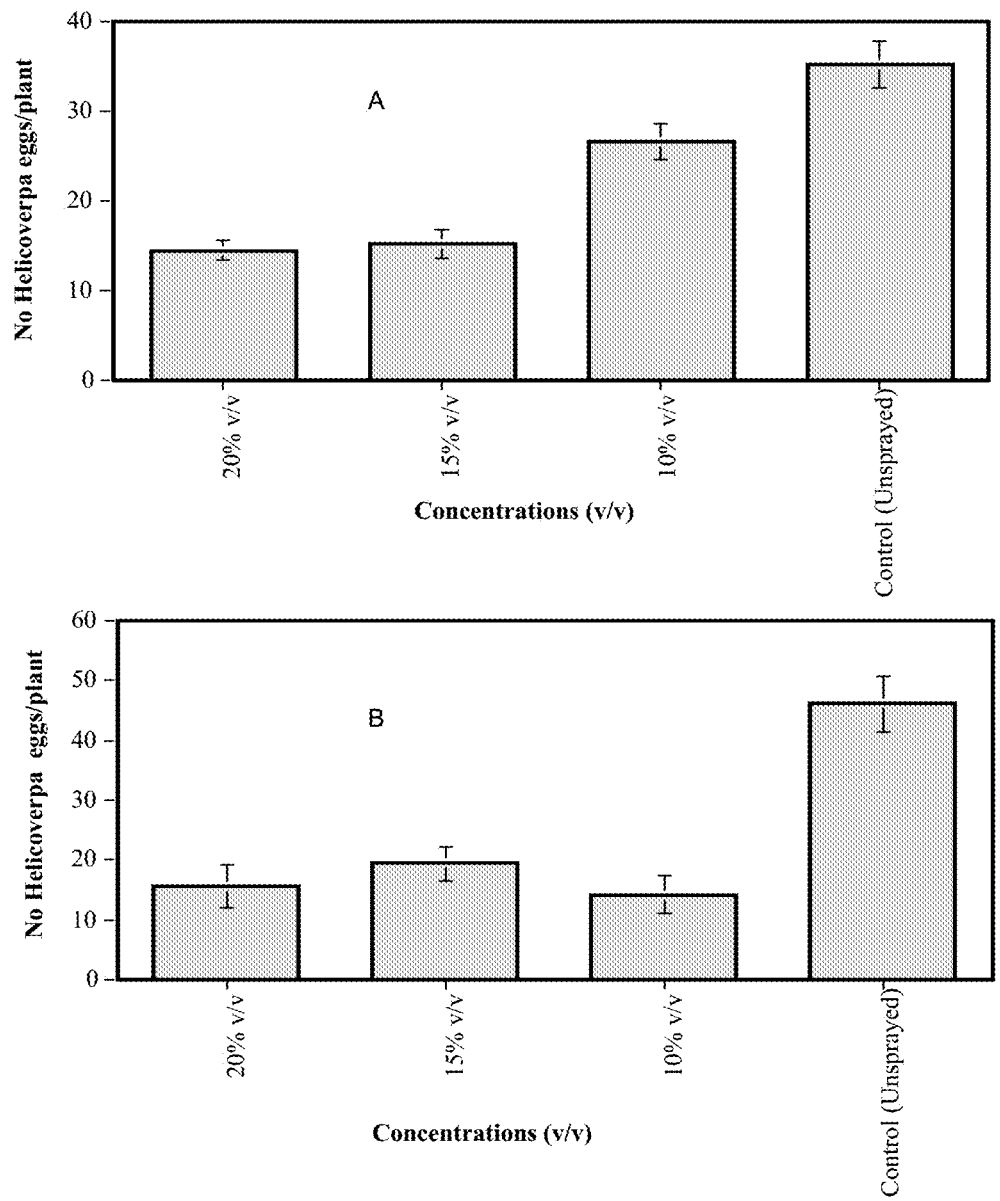
FIG. 6 is a graph illustrating the efficacy of combined *Clitoria ternatea* formulated in hexane on oviposition of *Helicoverpa* spp. on cotton plants.

The results of the study showed that the number of eggs per meter recorded on cotton plants treated with combined *Clitoria ternatea* fractions at 10%, 15% and 20% v/v were significantly lower (P<0.001) than the untreated (control) plants in all 3 experiments conducted (FIGS. 6a,b and 7). No significant difference (P>0.05) was detected among the *Clitoria ternatea* concentrations indicating 10% v/v concentration was as efficacious as the 15 and 20% v/v concentrations (FIGS. 6A,B and 7). It was also observed that the Hexane formulation was toxic to the cotton plants causing burns on the leaves.

EXAMPLE 8

Field Experiments with *Clitoria ternatea* Fractions—Effect of Combined *Clitoria ternatea* Fractions Formulated in Hexane on Oviposition of *Helicoverpa* Spp. on Cotton Plants

*Clitoria ternatea* formulations 2, 3 and 4 were formulated in hexane and used for field trials on conventional cotton crops against *Helicoverpa* spp. The trial was conducted on commercial conventional cotton crops. The *Clitoria ternatea* formulation was evaluated at 3 different concentrations (1) 20% v/v (2) 15% v/v (3) 10% v/v and (4) Control (Unsprayed) for efficacy against *Helicoverpa* spp. eggs and larvae. Each treatment was replicated 4 times in a randomised complete block design. Each replicate or treated plot measured 100 meters long and 6 meters or rows wide. Foliar application of the different rates of the formulated *Clitoria ternatea* fractions was applied in 15 liters of water twice during the trial 24 days apart. *Helicoverpa* spp. eggs and larvae were assessed visually on one meter row of randomly selected cotton plants. Pre-treatment counts were taken one day before treatment application, and post-treatment counts 7, 14, 21 and 28 days after treatment. Data was expressed as number of *Helicoverpa* spp. eggs and larvae per meter per sample date.

Analysis of Data

All experimental data were analysed using repeated measures ANOVA (Graphpad Instat Software, Inc., v2.03, San Diego, Calif., USA). Treatment and sample dates were the independent variables. Tukey-Kramer Multiple Comparisons test was used to separate the means.

Results

Figure 8:
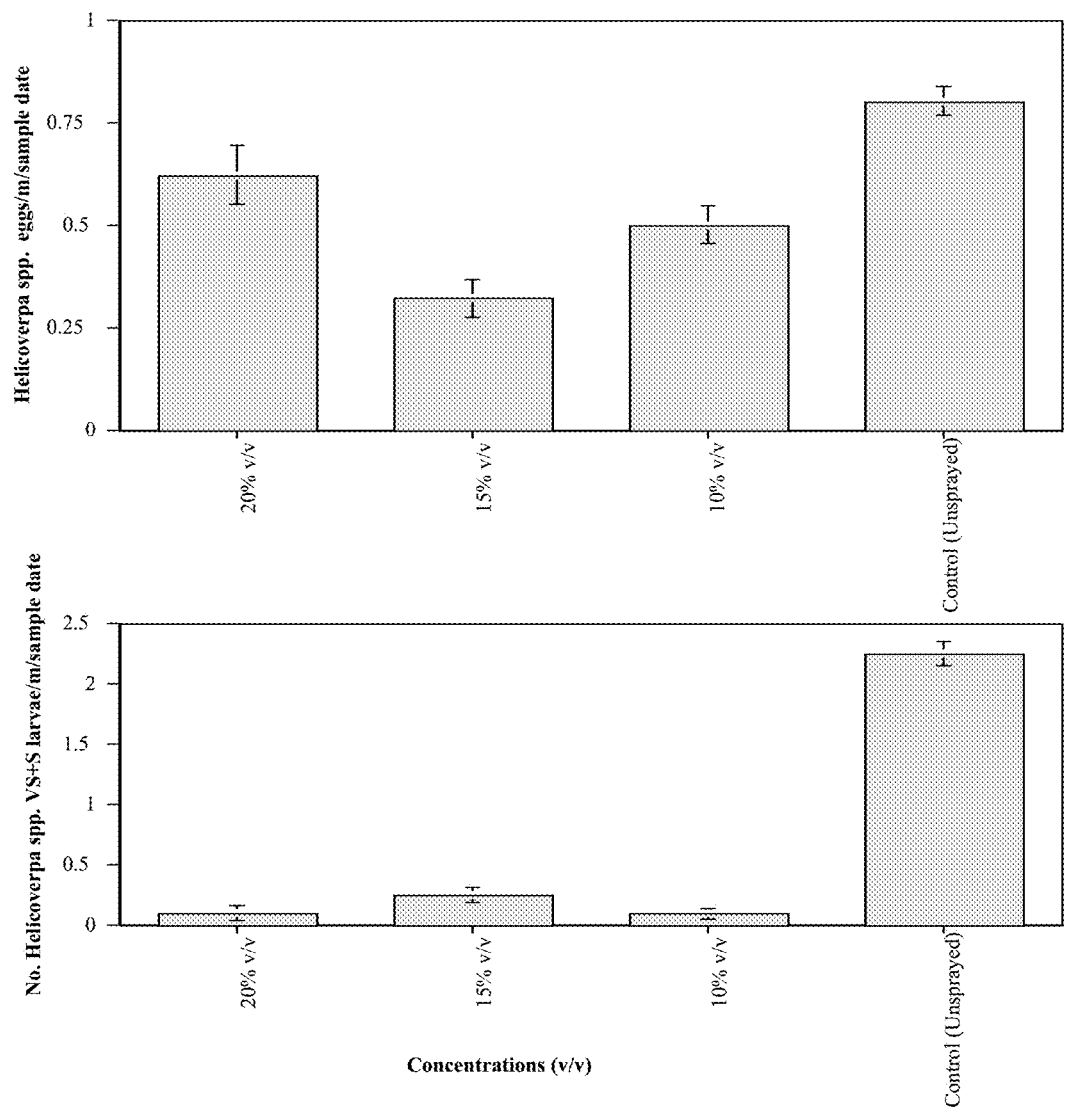
FIG. 8 shows the efficacy of different concentrations of *Clitoria ternatea* formulated in hexane on the number of *Helicoverpa* spp. eggs and larvae per meter per sample date recorded on commercial conventional cotton fields.

A significant difference (P<0.001) was found among cotton plants treated with *Clitoria ternatea* fractions and the untreated (control) plants (FIG. 8). However, no significant difference (P>0.05) was detected in oviposition deterrent activity between the *Clitoria ternatea* concentrations (FIG. 8).

Figure 7:
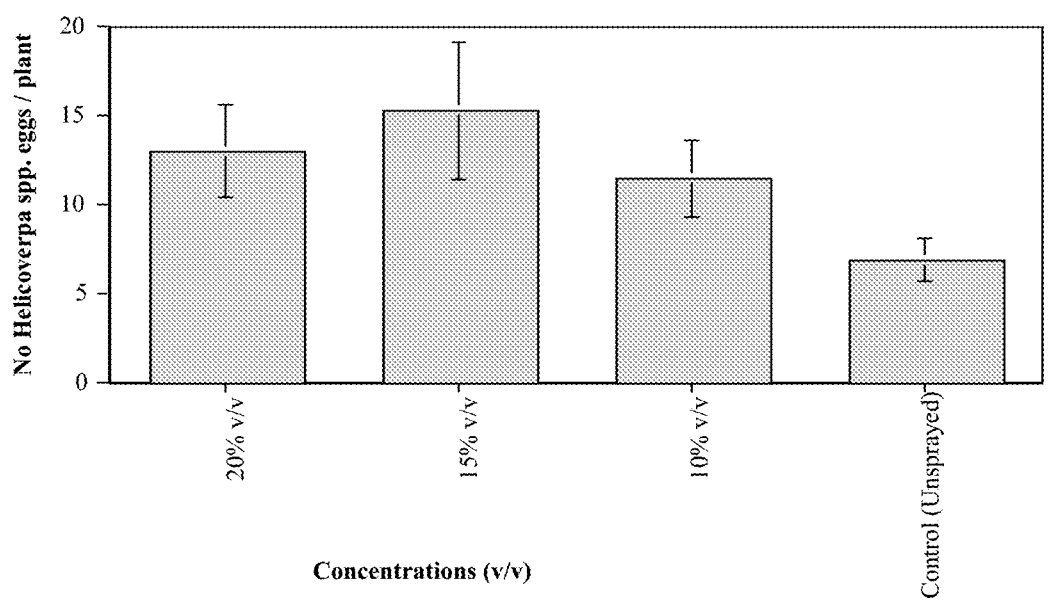
FIG. 7 shows the efficacy of different concentrations of *Clitoria ternatea* formulated in hexane on oviposition of *Helicoverpa* spp. on cotton plants.

The number of *Helicoverpa* spp. very small and small ($1^{st}$ $3^{rd}$ instar) larvae per meter per sample date recorded on plots treated with different concentrations of *Clitoria ternatea* were significantly lower (P<0.001) than the untreated (control) plots (FIG. 7). However, no significant difference (P>0.05) was found among the different concentrations of the *Clitoria ternatea* products tested (FIG. 8).

EXAMPLE 9

Efficacy of *Clitoria ternatea* Formulations on Oviposition of *Helicoverpa armigera* Females on Cotton Plants in the Mesh House The oviposition response of mated *Helicoverpa* spp. to potted cotton plants treated with different concentrations of *Clitoria ternatea* in Canola oil and Crude cotton seed oil was evaluated. The plants used in the study were potted squaring cotton plants of the same age. The experiment was conducted under no-choice conditions. The treatments evaluated were (1) 1% *Clitoria ternatea* in Canola oil, (2) 2% *Clitoria ternatea* in Canola, (3) 1% *Clitoria ternatea* in crude Cotton seed oil, (4) 2% *Clitoria ternatea* in crude cotton seed oil and (5) Control (water). Each treatment was replicated 8 times with each treatment containing 10 plants. Each treatment was applied to the respective cotton plants until run-off. Each treatment replicate of 10 plants were enclosed in a plastic cage containing 4 mated *H. armigera* female to oviposit on the plants. Four days after treatment, the eggs on each plant was counted and recorded. Data was expressed as number of eggs per plant.

Analysis of Data

All experimental data were analysed using the ANOVA procedures of Instat, version 2.03 (Graphpad Instat Software Inc., San Diego, Calif., USA). Tukey-Kramer multiple comparison tests were used to separate the means.

Results

No significant difference in the number of eggs per plant was detected among plants treated with the different *Clitoria ternatea* formulations (Table 3). However significant differences in the number of eggs per plant were detected between the treated and the control plants (Table 3). Significantly higher (P<0.0001) eggs per plant was recorded on the control plants compared to the *Clitoria ternatea*—Oil formulations (Table 3).

TABLE 3

Effect of *Clitoria ternatea* in oil formulation on oviposition of *H. armigera*. (replicates per treatment) (n = 100 mated pairs of *H. armigera* females).

| Treatments | No. eggs per plant |
| --- | --- |
| 1% *Clitoria ternatea* + Canola oil | 18.25 ± 3.16 a |
| 2% *Clitoria ternatea* + Canola oil | 21.13 ± 1.84 a |
| 1% *Clitoria ternatea* + Cotton seed oil | 21.38 ± 3.06 a |

TABLE 3-continued

Effect of *Clitoria ternatea* in oil formulation
on oviposition of *H. armigera*. (replicates per
treatment) (n = 100 mated pairs of *H. armigera* females).

| Treatments | No. eggs per plant |
| --- | --- |
| 2% *Clitoria ternatea* + crude cotton seed oil | 18.63 ± 2.87 a |
| Control (Unsprayed) | 37.88 ± 3.62 b |

Means between treatments followed by the same letters are not significantly different (P > 0.05) by Tukey-Kramer Multiple comparison test

EXAMPLE 10

Effect of *Clitoria ternatea* Formulations on Mortalities of *H. armigera* Larvae in the Laboratory The study was conducted on *Helicoverpa* spp. artificial diet in the laboratory at ACRI. During this experiment the laboratory was maintained at a temperature of 25° C. and a relative humidity of 55-60%. The treatments evaluated were (1) 1% v/v *Clitoria ternatea* in Cotton seed oil, (2) 1% v/v *Clitoria ternatea* in crude cotton seed oil, (3) 1% v/v *Clitoria ternatea* in Canola oil and (4) Control (water). For each concentration, I sprayed a total of 48 2nd instar larvae (12 larvae/replicate) until run off. After spray application, larvae from each treatment were transferred and kept separately in 35 mL clear plastic containers (P10M; Solo, Urbana, Illionis, USA) containing a soybean-based artificial diet mixed individually with each treatment. Each treatment was replicated 4 times. The number of dead larvae were counted and recorded in each treatment at 14 days after treatment when all larvae in the control had pupated.

Analysis of Data

All experimental data were analysed using the ANOVA procedures of Instat, version 2.03 (Graphpad Instat Software Inc., San Diego, Calif., USA). Tukey-Kramer multiple comparison tests were used to separate the means.

Results

Figure 9:
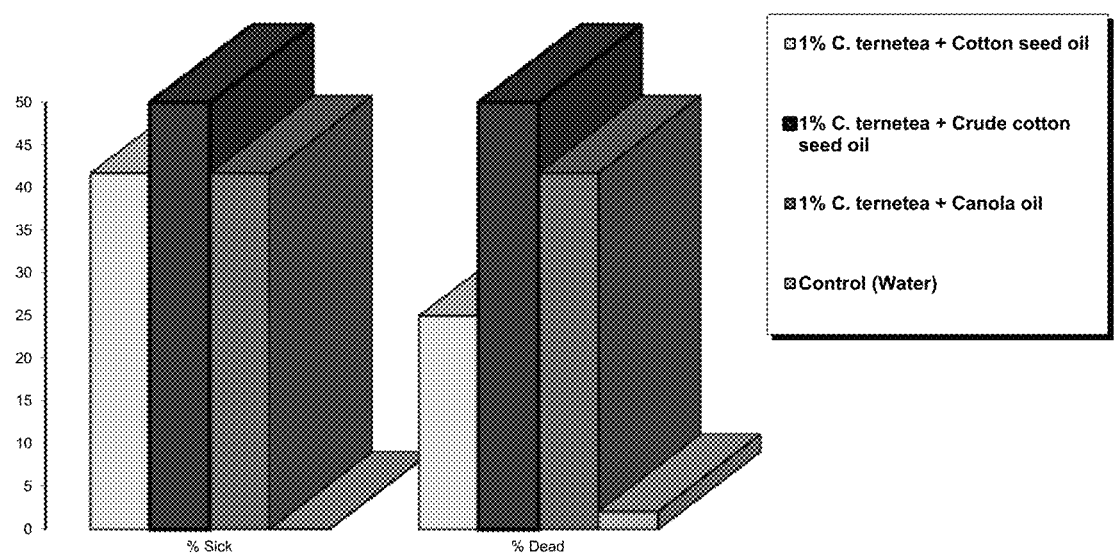
FIG. 9 shows the efficacy of *Clitoria ternatea* formulated in (1) cotton seed oil (2) crude cotton seed oil and (3) canola oil on *Helicoverpa* spp. larvae from $2^{nd}$ instar larvae until pupation on artificial diets.
Figure 10:
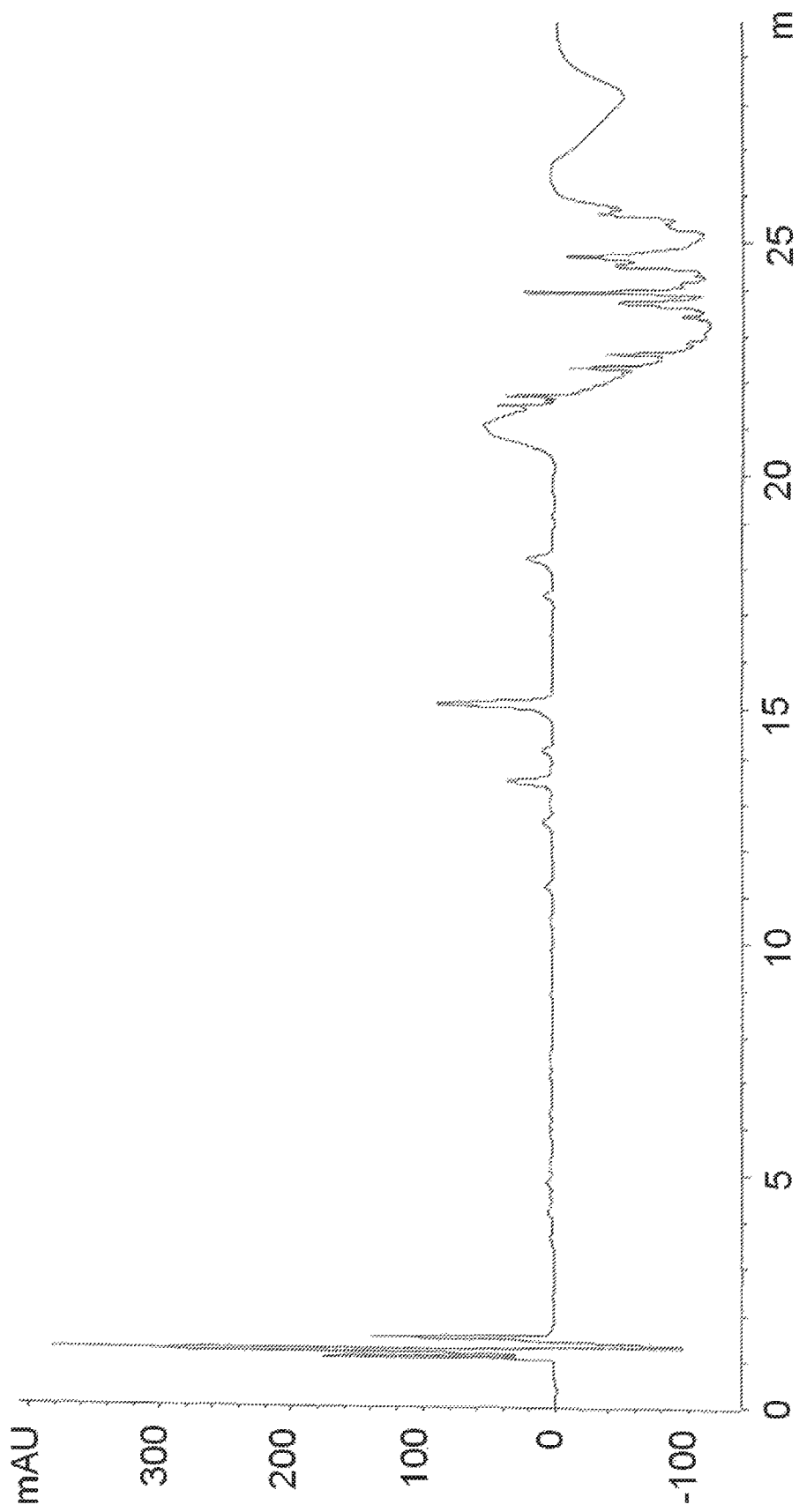
FIG. 10 is a HPLC profile at UV210 nm of a methanolic extraction of a composition comprising SPCs derived from *Clitoria ternatea* plant material at a pre-flower stage (comprising no flowers or pods) by contact with canola oil. The profile was obtained using an Agilent 1100 LCMSD with a Phenomex Luna C18 column at 40° C. using the following solvent gradient conditions.

At 14 DAT, the number of dead larvae was highest in the 1% v/v *Clitoria ternatea* in crude cotton seed oil, followed by 1% v/v *Clitoria ternatea* in canola and cotton seed oils (FIG. 9). No deaths were recorded in the larvae treated with water (control) (FIG. 9). Additionally, most of the larvae that were not dead in the *Clitoria ternatea* treated plots were sick and sluggish (FIG. 9). There were no sick larvae in the control and all larvae had pupated. Overall, the development of the *Clitoria ternatea* treated larvae was delayed by an average of 4 days relative to the control.

EXAMPLE 11

Efficacy of *Clitoria ternatea* Oil Formulations on Pests and Beneficial Insects in Conventional Cotton The study was conducted on late season commercial conventional cotton crop. The trial did not target any specific pest but treatments were applied to the cotton crops and evaluated for efficacy against any pest and predatory insects that were on the crop during that period of the cotton season in the lower Namoi region. The treatment evaluated were (1) 1% v/v *Clitoria ternatea* in Canola oil, (2) 2% v/v *Clitoria ternatea* in Canola oil, (3) 1% v/v *Clitoria ternatea* in Crude cotton seed oil, (4) 2% v/v *Clitoria ternatea* in Crude Cotton seed oil, (5) Unsprayed (control). Each treatment was replicated 3 times in a randomised complete block design. Each replicate measured 100 meters long and 6 rows or meters wide.

Foliar application of each treatment was made on day 1. Visual counts of the following pests green mirids (*Creontiades dilutus*), Cotton loopers (*Anomis flava*), Green vegetable bug (*Nezara viridula*) and Apple dimpling bug (*Campylomma liebknechti*), and predatory insects (predatory beetles, bugs, lacewings and spiders) which were abundant in the study site at the period of the trials in each treatment were made 24 hours before treatment and 3, 5 and 7 days after treatment. Counts were made in a two randomly selected 1 meter lengths of row of cotton in each treatment replicate, i.e. a total of 6 meters per treatment. Counts were separated into the various pests and predators. The beneficial insects were grouped into predatory beetles, bugs, lacewings and spiders. Data were expressed in numbers per meter.

Analysis of Data

All experimental data were analysed using repeated measures ANOVA (Graphpad Instat Software, Inc, v2.03, San Diego, Calif., USA). Treatment and sample dates were the independent variables. Tukey-Kramer Multiple comparisons tests were used to separate means.

Results

Predominant pests in the trial site during the trial period were green mirids, cotton loopers, green vegetable bugs and apple dimpling bugs. *Helicoverpa* spp. were absent at the trial site. Therefore, the data reported here are on those pests that were abundant during the test period.

Effect of *Clitoria ternatea* on Green Mirids

The number of green mirids per meter recorded in the study plots ranged from 0.17 to 0.33 per meter (Table 4). At 3 DAT, all the *Clitoria ternatea* treated plots had no mirids recorded in them whereas the unsprayed plot recorded 0.33 per meter (Table 4). At 5 DAT, the number of mirids per meter recorded in plots treated with 2% v/v *Clitoria ternatea* were significantly different (P<0.01) than unsprayed plots but were not significantly different (P>0.05) from plots treated with 1% v/v *Clitoria ternatea* (Table 4). The number of green mirids recorded on plots treated with 1% v/v *Clitoria ternatea* was not significantly different from the unsprayed (control) plots at 5 DAT (Table 4). At 7 DAT, number of green mirids per meter recorded on treated and control; plots were not significantly different (Table 4). This may be due to hatching of mirid eggs that were laid on the plants pre-treatment and also lack of good coverage of the products as many of the plants were dislodged as a result of the heavy boll load.

Effect of *Clitoria ternatea* on Cotton Loopers

They were the most abundant insect species on the cotton crop at the study site during the trials. The study showed that significantly lower (P<0.05) cotton loopers per meter were recorded on *Clitoria ternatea* treated plots compared to the control (Table 5). At 3 DAT, Cotton looper mortalities was highest on plots treated with 2% *Clitoria ternatea* in Crude cotton seed oil (58.9%), followed by 1% *Clitoria ternatea* in crude cotton seed oil (47.2%) (Table 5). The 1 and 2% *Clitoria ternatea* in Canola seed oils caused 26.6 and 42.9% mortalities respectively (Table 5). The unsprayed plot recorded a 10% increase in Cotton looper population at the same time (Table 5).

TABLE 4

Efficacy of different rates of *Clitoria ternatea* on the number of green mirids per metre recorded on commercial cotton crops

| Treatments | Pre-treatment | 3 DAT | 5 DAT | 7 DAT |
|---|---|---|---|---|
| 1% *Clitoria ternatea* + Canola oil | 0.17 ± 0.17 a | 0.00 ± 0.00 a | 0.33 ± 0.21ab | 0.33 ± 0.21a |
| 2% *Clitoria ternatea* + Canola oil | 0.17 ± 0.17 a | 0.00 ± 0.00 a | 0.17 ± 0.17 a | 0.17 ± 0.17a |
| 1% *Clitoria ternatea* + Crude Cotton oil | 0.33 ± 0.21 a | 0.00 ± 0.00 a | 0.33 ± 0.21ab | 0.33 ± 0.21a |
| 2% *Clitoria ternatea* + Crude Cotton oil | 0.17 ± 0.17 a | 0.00 ± 0.00a | 0.17 ± 0.17 a | 0.00 ± 0.00a |
| Control (Unsprayed) | 0.17 ± 0.17 a | 0.33 ± 0.21 b | 0.50 ± 0.22 b | 0.33 ± 0.21a |

Means within columns followed by same letters are not significantly different (P > 0.05) (Tukey-Kramer Multiple Comparison Test).

TABLE 5

Efficacy of different rates of *Clitoria ternatea* on the number of Cotton Looper (*Anomis flava*) per metre recorded on commercial cotton crops

| Treatments | Pre-treatment | 3 DAT | 5 DAT | 7 DAT |
|---|---|---|---|---|
| 1% *Clitoria ternatea* + Canola oil | 5.00 ± 1.16 a | 3.67 ± 0.76 a | 4.33 ± 0.96 a | 5.83 ± 0.95a |
| 2% *Clitoria ternatea* + Canola oil | 5.83 ± 0.91 a | 3.33 ± 1.02 a | 3.00 ± 0.68 a | 3.33 ± 0.62a |
| 1% *Clitoria ternatea* + Crude Cotton oil | 6.00 ± 1.48 a | 3.17 ± 0.87 a | 3.67 ± 0.88 a | 3.83 ± 1.33a |
| 2% *Clitoria ternatea* + Crude Cotton oil | 5.67 ± 1.09 a | 2.33 ± 0.67a | 3.83 ± 0.75 a | 2.67 ± 0.80a |
| Control (Unsprayed) | 8.33 ± 1.41a | 9.17 ± 1.72 b | 6.83 ± 1.92 a | 7.17 ± 0.83a |

Means within columns followed by same letters are not significantly different (P > 0.05) (Tukey-Kramer Multiple Comparison Test).

Effect of *Clitoria ternatea* on Apple Dimpling Bug

The *Clitoria ternatea* formulation at different concentrations had significant effect on ADB population in the study site at 3 DAT (Table 6). The highest ADB kill at 3 DAT was recorded in plots treated with 2% *Clitoria ternatea* in Crude cotton seed oil (65.9%), followed by 2% *Clitoria ternatea* in Canola oil (64.0%) (Table 6). The 1% *Clitoria ternatea* in Canola and crude cotton seed oils recorded 56.8 and 52.1% mortalities respectively at 3 DAT (Table 6).

TABLE 6

Efficacy of different rates of Clitoria ternatea on the number of Apple Dimpling bugs (*Campylomma liebknechti*) per metre recorded on commercial cotton crops

| Treatments | Pre-treatment | 3 DAT | 5 DAT | 7 DAT |
|---|---|---|---|---|
| 1% *Clitoria ternatea* + Canola oil | 4.67 ± 0.84 a | 0.67 ± 0.33 a | 0.50 ± 0.22ab | 0.33 ± 0.21a |
| 2% *Clitoria ternatea* + Canola oil | 2.67 ± 0.42 a | 0.50 ± 0.22 a | 0.00 ± 0.00 a | 0.00 ± 0.00a |
| 1% *Clitoria ternatea* + Crude Cotton oil | 3.33 ± 0.84 a | 0.83 ± 0.31 a | 0.17 ± 0.17 a | 0.33 ± 0.21a |
| 2% *Clitoria ternatea* + Crude Cotton oil | 4.67 ± 0.65 a | 0.83 ± 0.31a | 0.17 ± 0.17 a | 0.00 ± 0.00a |
| Control (Unsprayed) | 4.17 ± 0.70 a | 2.17 ± 0.31 b | 1.00 ± 0.26 b | 0.83 ± 0.17a |

Means within columns followed by same letters are not significantly different (P > 0.05) (Tukey-Kramer Multiple Comparison Test)

Beneficial Insects

Beneficial insects identified from the treated plots were predominantly predators and these include predatory beetles, bugs, lacewings and spiders (Table 7).

TABLE 7

Predators of cotton pests sampled and identified from study plots.

| Order | Family | Species | Group |
|---|---|---|---|
| Coleoptera | Coccinellidae | *Coccinella transversalis* (Fabricius) | Predatory beetles |
| | | *Diomus notescens* (Blackburn) | |
| | Melyridae | *Dicranolauis bellulus* (Guerin-Meneville) | |
| Hemiptera | Nabidae | *Nabis capsiformis* (Germar) | Predatory bugs |
| | Lygaeidae | *Geocoris lubra* (Kirkaldy) | |
| | Pentatomidae | *Cermatulus nasalis* (Westwood) | |

TABLE 7-continued

Predators of cotton pests sampled and identified from study plots.

| Order | Family | Species | Group |
|---|---|---|---|
| | | *Ochelia schellenbergii* (Guerin-Meneville) | |
| | | *Coranus triabeatus* (Horvath) | |
| Neuroptera | Chrysopidae | *Chrysopa* spp. | Predatory lacewings |
| | Hemerobiidae | *Micromus tasmaniae* (walker) | |
| Araneida | Lycosidae | *Lycosa* spp. | spiders |
| | Oxyopidae | *Oxyopes* spp. | |
| | Salticidae | Salticidae spp. | |
| | Araneidae | *Araneus* spp. | |

No significant difference was detected among the treatments and control in the number of predatory beetles (Table 8), bugs (Table 9), lacewings (Table 10) and spiders (Table 11). This indicates that *Clitoria ternatea* products have no effect on beneficial insects in cotton.

TABLE 8

Efficacy of different rates of *Clitoria ternatea* application on the number of predatory beetles per metre on commercial conventional cotton crops.

| Treatments | Pre-treatment | 3 DAT | 5 DAT | 7 DAT |
|---|---|---|---|---|
| 1% *Clitoria ternatea* + Canola oil | 0.50 ± 0.22 a | 1.17 ± 0.48 a | 1.00 ± 0.37 a | 0.67 ± 0.21a |
| 2% *Clitoria ternatea* + Canola oil | 1.33 ± 0.42 a | 1.33 ± 0.49 a | 0.83 ± 0.31 a | 1.33 ± 0.21a |
| 1% *Clitoria ternatea* + Crude Cotton oil | 1.00 ± 0.26 a | 1.17 ± 0.31 a | 1.83 ± 0.70 a | 1.00 ± 0.21a |
| 2% *Clitoria ternatea* + Crude Cotton oil | 0.67 ± 0.21 a | 1.33 ± 0.33 a | 0.87 ± 0.21 a | 0.67 ± 0.00a |
| Control (Unsprayed) | 0.67 ± 0.21 a | 2.17 ± 0.17 a | 2.83 ± 0.87 a | 1.67 ± 0.22a |

Means within columns followed by same letters are not significantly different ($P > 0.05$) (Tukey - Kramer Multiple Comparison Test)

TABLE 9

Efficacy of different rates of *Clitoria ternatea* application on the number of predatory bugs per metre on commercial conventional cotton crops.

| Treatments | Pre-treatment | 3 DAT | 5 DAT | 7 DAT |
|---|---|---|---|---|
| 1% *Clitoria ternatea* + Canola oil | 1.00 ± 0.37 a | 2.17 ± 0.40 a | 2.33 ± 0.33 a | 2.17 ± 0.48a |
| 2% *Clitoria ternatea* + Canola oil | 0.83 ± 0.31 a | 2.50 ± 0.43 a | 2.83 ± 0.48 a | 2.17 ± 0.31a |
| 1% *Clitoria ternatea* + Crude Cotton oil | 1.00 ± 0.37 a | 2.33 ± 0.33 a | 2.67 ± 0.62 a | 2.00 ± 0.31a |
| 2% *Clitoria ternatea* + Crude Cotton oil | 0.83 ± 0.31 a | 1.33 ± 0.21 a | 1.83 ± 0.48 a | 2.33 ± 0.33a |
| Control (Unsprayed) | 1.50 ± 0.43 a | 2.50 ± 0.34 a | 2.67 ± 0.42 a | 4.17 ± 0.26a |

Means within columns followed by same letters are not significantly different ($P > 0.05$) (Tukey - Kramer Multiple Comparison Test)

TABLE 10

Efficacy of different rates of *Clitoria ternatea* application on the number of predatory lacewings per metre on commercial conventional cotton crops.

| Treatments | Pre-treatment | 3 DAT | 5 DAT | 7 DAT |
|---|---|---|---|---|
| 1% *Clitoria ternatea* + Canola oil | 0.50 ± 0.22 a | 1.00 ± 0.26 a | 0.83 ± 0.17 a | 0.50 ± 0.22a |
| 2% *Clitoria ternatea* + Canola oil | 0.33 ± 0.21 a | 1.50 ± 0.43 a | 1.00 ± 0.26 a | 0.33 ± 0.21a |
| 1% *Clitoria ternatea* + Crude Cotton oil | 0.33 ± 0.21 a | 1.67 ± 0.42 a | 0.83 ± 0.31 a | 0.50 ± 0.22a |

TABLE 10-continued

Efficacy of different rates of *Clitoria ternatea* application on the number of predatory lacewings per metre on commercial conventional cotton crops.

| Treatments | Pre-treatment | 3 DAT | 5 DAT | 7 DAT |
|---|---|---|---|---|
| 2% *Clitoria ternatea* + Crude Cotton oil | 0.50 ± 0.22 a | 0.67 ± 0.33 a | 1.00 ± 0.26 a | 0.33 ± 0.21a |
| Control (Unsprayed) | 0.67 ± 0.21 a | 0.83 ± 0.31 a | 0.83 ± 0.33 a | 0.50 ± 0.34a |

Means within columns followed by same letters are not significantly different (P > 0.05) (Tukey - Kramer Multiple Comparison Test)

TABLE 11

Efficacy of different rates of *Clitoria ternatea* application on the number of spiders per metre on commercial conventional cotton crops.

| Treatments | Pre-treatment | 3 DAT | 5 DAT | 7 DAT |
|---|---|---|---|---|
| 1% *Clitoria ternatea* + Canola oil | 6.33 ± 1.54 a | 3.50 ± 1.15 a | 3.00 ± 0.78 a | 4.17 ± 0.60a |
| 2% *Clitoria ternatea* + Canola oil | 3.00 ± 0.68 a | 3.33 ± 0.56 a | 3.33 ± 0.67 a | 2.33 ± 0.72a |
| 1% *Clitoria ternatea* + Crude Cotton oil | 5.17 ± 0.79 a | 2.50 ± 0.43 a | 2.83 ± 0.83 a | 3.17 ± 0.40a |
| 2% *Clitoria ternatea* + Crude Cotton oil | 3.67 ± 0.84 a | 3.00 ± 1.00 a | 2.00 ± 0.68 a | 2.83 ± 0.60a |
| Control (Unsprayed) | 5.67 ± 0.95 a | 4.17 ± 0.87 a | 3.17 ± 1.07 a | 3.17 ± 0.91a |

Means within columns followed by same letters are not significantly different (P > 0.05) (Tukey - Kramer Multiple Comparison Test)

EXAMPLE 12

Formulation of *Clitoria ternatea* for Laboratory Trials Against Cotton Pests

*Clitoria ternatea* material was harvested at different growth stages at three different locations. The extracts were made by heating dry, macerated plant (30 g for each solvent) in an 80° C. water bath for 1 hour. Filtration and evaporation were carried out after 24 hours. The solutions were evaporated under vacuum at 400° C., while the evaporation of the water solution was performed using the water bath. The solutions were evaporated until fractionalized concentrates were obtained. The fractionalized concentrates were formulated in surfactants (C12-C15 Ethoxylate and Teric® (Huntsman), an emulsifier (Termul® 3000) and a light molecular weight oil such as crude cotton seed oil, refined cotton seed oil and canola oil. Vacuum and pressure was applied to ensure efficient filtration.

Four formulations were developed for use in laboratory and field bioassays against cotton pests and beneficial insects. The formulations were:
(1) *Clitoria ternatea* formulation in oil without emulsifiers (Formulation A),
(2) Formulation with emulsifiers but without *Clitoria ternatea* (Formulation B),
(3) *Clitoria ternatea* formulations with emulsifiers (Formulation C) and
(4) *Clitoria ternatea* formulations with emulsifiers (Formulation D).

Effect of Different Rates of *Clitoria ternatea* on Mortalities of Green Mirids in the Laboratory The four formulations were evaluated at 0.5%, 1.0%, 1.5% and 2.0% (v/v) in the laboratory at a temperature of 25° C. and relative humidity of 55-60%. Water was used as control. For each formulation, a total of 6 (3 pairs) adult female and male mirids per treatment (1 pair/replicate) on beans were sprayed until run off. In addition the beans were also dipped for 60 seconds in each treatment. After treatment applications, a pair of green mirids (male and female) were transferred and released on dipped beans kept separately in 35 mL clear plastic containers (P101M; Solo, Urbana, Illionis, USA). Each treatment was replicated 3 times. The number of dead mirid adults were counted and recorded daily until all insects in the most efficacious treatment die. The percent mortality was calculated relative to the control.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

Results

Significant differences (P<0.01) were detected among treatments (Table 12). Fewer mirids were killed when *Clitoria ternatea* was applied at 0.5% v/v. As the rate of application increased the number of green mirids killed increased significantly (Table 12). Formulation A caused the highest mortalities to green mirid adults at all the rates tested (Table 12). At 1% v/v rate Formulation A caused 55.7% mortality compared to 44.3% caused by Formulation C and Formulation D respectively (Table 12). The highest mortality was caused by Formulation A (100%), Formulation C (89%) and Formulation D (100%) when the products were applied at 2% v/v rate (Table 12). The mortality to green mirids caused by Formulation B which did not contain *Clitoria ternatea* was significantly lower (P<0.01) than the other formulations containing *Clitoria ternatea*, and was not significantly different from the insects treated with water (control) (Table 12).

TABLE 12

Effect of direct spray application and residues of canola-oil based *Clitoria ternatea* on mortalities of green mirid adults in the laboratory.

| Treatments | 0.5% v/v (% mortality) | 1.0% v/v (% mortality) | 1.5% v/v (% mortality) | 2.0% v/v (% mortality) |
|---|---|---|---|---|
| Formulation A | 2.00 ± 0.58 a (33.3%) | 1.33 ± 0.33 a (55.7%) | 0.33 ± 0.33 a (89.0%) | 0.00 ± 0.00 a (100.0%) |
| Formulation B | 2.67 ± 0.33 b (11.0%) | 2.67 ± 0.33 b (11.0%) | 2.67 ± 0.33 b (11.0%) | 2.67 ± 0.33 b (11.0%) |
| Formulation C | 2.00 ± 0.58 a (33.3%) | 1.67 ± 0.67 a (44.3%) | 1.67 ± 0.33 a (44.3%) | 0.33 ± 0.33 a (89.0%) |
| Formulation D | 2.33 ± 0.33 a (22.3%) | 1.67 ± 0.33 a (44.3%) | 1.33 ± 0.33 a (55.7%) | 0.00 ± 0.00 a (100.0%) |
| Water (control) | 3.00 ± 0.33 b | 3.00 ± 0.33 b | 3.00 ± 0.33 b | 3.00 ± 0.33 b |
| Level of significance | P < 0.01 | P < 0.001 | P < 0.01 | P < 0.01 |

Means between treatments within columns followed by the same letter are not significantly different (P > 0.05); Tukey-Kramer multiple comparison test.

EXAMPLE 13

Efficacy of Combination of Direct Application and Residues of *Clitoria ternatea* on Survival of Green Mirid Adults The *Clitoria ternatea* formulations Formulation A, Formulation C and Formulation D were evaluated at 1 and 2 L/ha in the laboratory with temperature at 25° C. and 60-70% RH. Water was used as a control. For each formulation, a total of 6 (3 pairs) adult female and male mirids per treatment (1 pair/replicate) were sprayed on beans until run off. The beans were also dipped for 60 seconds in each formulation and transferred and kept separately in 35 mL clear plastic containers (P101M; Solo, Urbana, Illionis, USA). Thereafter, one male and female green mirids (a pair) were released onto the beans in the plastic containers. Each treatment was replicated 3 times. The number of dead mirid adults (males and females) were counted and recorded at 3, 5, 7, 9 and 11 days after treatment and the percent mortality was calculated relative to the control.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

Results

Efficacy on Mortality of Green Mirid Adult Males

At 3 DAT, none of the *Clitoria ternatea* treatments caused mortalities to green mirid adult males exception of 2 L/ha Formulation A that caused 33.3% mortality (Table 13). At 5 DAT, Formulation D and Formulation A applied at 2 L/ha caused 33.3% mortality whereas the lower rates of *Clitoria ternatea* products did not kill any mirid. The 1 L/ha rate of the *Clitoria ternatea* products caused 33.3% mortality of green mirids at 7 DAT whereas the 2 L/ha rate caused 66.7% (Table 13). At 9 and 11 DAT, 2 L/ha Formulation A and Formulation D caused 100% kill of the mirids whereas the 1 L/ha rates and 2 L/ha Formulation C caused 66.7% kill (Table 13).

TABLE 13

Effect of *Clitoria ternatea* residues on mortalities of green mirid adult in the laboratory

| Treatments | Pre-treatment | 3 DAT % mortality | 5 DAT % mortality | 7 DAT % mortality | 9 DAT % mortality | 11 DAT % mortality |
|---|---|---|---|---|---|---|
| 1 L/ha Formulation C | 0 | 0a | 0a | 33.33a | 66.67a | 66.67a |
| 1 L/ha Formulation D | 0 | 0a | 0a | 33.33a | 66.67a | 100.00b |
| 1 L/ha Formulation A | 0 | 0a | 0a | 33.33a | 66.67a | 100.00b |
| 2 L/ha Formulation C | 0 | 0a | 0a | 33.33a | 66.67a | 100.00b |
| 2 L/ha Formulation D | 0 | 0a | 33.33a | 66.67b | 100.00b | 100.00b |
| 2 L/ha Formulation A | 0 | 33.33a | 33.33a | 66.67b | 100.00b | 100.00b |
| Control (water) | 0 | 0a | 0a | 0c | 0c | 0c |

Means between treatments within columns followed by the same letter are not significantly different (P > 0.05); Tukey-Kramer multiple comparison test.

EXAMPLE 14

Efficacy on Mortality of Green Mirid Adult Females

The mortality of green mirid adult females at 3 DAT was zero but was 33.3% at 5 DAT (Table 14). The mortality when the female adults and beans were treated with 2 L/ha Formulation A and Formulation D was 66.7% at 7 DAT compared to 33.3% when they were treated with 1 L/ha Formulation D and Formulation A (Table 14). None of the insects treated with 1 L/ha Formulation C were dead at 7 DAT and only 33.3% died at 9 and 11 DAT. In contrast, application of 2 L/ha Formulation A and Formulation D killed 100 percent of the female adults at 9 DAT, whereas the 2 L/ha Formulation C killed 77.7% and the 1 L/ha Formulation D and Formulation A killed 66.7% of the insects. At 11 DAT, all the treated insects have died with the exception of insects treated with 1 L/ha Formulation C and 1 L/ha Formulation D where only 33.3 and 66.7% respectively died (Table 14).

Data was expressed as number of eggs laid per female and compared among the treatments.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

TABLE 14

Effect of *Clitoria ternatea* residues on mortalities of green mirid adult females in the laboratory

| Treatments | Pre-treatment | 3 DAT % mortality | 5 DAT % mortality | 7 DAT % mortality | 9 DAT % mortality | 11 DAT % mortality |
|---|---|---|---|---|---|---|
| 1 L/ha Formulation C | 0 | 0 | 0 b | 0 a | 33.33a | 33.33a |
| 1 L/ha Formulation D | 0 | 0 | 33.33a | 33.33b | 66.67b | 66.67b |
| 1 L/ha Formulation A | 0 | 0 | 33.33a | 33.33b | 66.67b | 100.00c |
| 2 L/ha Formulation C | 0 | 0 | 33.33a | 66.67 c | 77.70b | 100.00c |
| 2 L/ha Formulation D | 0 | 0 | 33.33a | 66.67c | 100.00c | 100.00c |
| 2 L/ha Formulation A | 0 | 0 | 33.33a | 66.67c | 100.00c | 100.00c |
| Control (water) | 0 | 0 | 0b | 0a | 0d | 0d |

Means between treatments within columns followed by the same letter are not significantly different (P > 0.05); Tukey-Kramer multiple comparison test.

EXAMPLE 15

Oviposition Deterrent Activity of *Clitoria Ternatea* on Green Mirid Adults on Beans in the Laboratory: Effect on Total Egg Lay The *Clitoria ternatea* formulations Formulation A, Formulation B, Formulation C and Formulation D were evaluated at 0.5%, 1.0%, 1.5% and 2.0% (v/v) in the laboratory with 25° C. temperature and 40% RH. Water was used as a control. For each formulation, a total of 6 (3 pairs) green mirid adult females and males mirids per treatment (1 pair/replicate) were sprayed on filter papers until run off. Beans were dipped for 60 seconds in each formulation and then transferred and kept separately in 35-mL clear plastic containers (P101M; Solo, Urbana, Illionis, USA). Three pairs of treated green mirid adults were released onto the treated beans in each plastic container. Each treatment was replicated 4 times. The number of eggs were counted under a binocular microscope and recorded daily until 9 days after treatment when all the insects in one of the treatments died.

Results

Oviposition of green mirids on beans were significantly lower (P<0.001) at all concentrations in insects treated with Formulation A than the other treatments and control (Table 15). At 0.5% v/v *Clitoria ternatea* extract, 1.17 eggs/female was laid on beans treated with Formulation A compared to 8.58 and 7.25 per female respectively in Formulation C and Formulation D treated plants (Table 15). The Formulation B and the unsprayed beans had 11 and 12.42 eggs/female respectively (Table 15). At 1.0% v/v, the number of eggs laid per female on the insects and beans treated with Formulation D were the same as Formulation A, Formulation B and Formulation C but Formulation A was different from Formulation B and Formulation C. The number of eggs recorded per female on Formulation A and Formulation D treated plants were significantly lower (P<0.0009) than the control (Table 15). At 1.5 and 2 L/ha rates, no significant differences was detected in the number of eggs per female in Formulation A, Formulation C and Formulation D treated insects and beans. However, the number of eggs per female on Formulation A treated insects and beans were significantly lower (P<0.005 and P<0.01) than Formulation B and the unsprayed (control) (Table 15).

TABLE 15

Effect of direct spray application and residues of *Clitoria ternatea* formulations on oviposition of green mirid adults on beans in the laboratory.

| Treatments | 0.5% v/v | 1.0% v/v | 1.5% v/v | 2.0% v/v |
|---|---|---|---|---|
| Formulation A | 1.17 ± 0.44 a | 1.35 ± 0.65 a | 1.25 ± 1.33 a | 2.00 ± 1.00 a |
| Formulation B | 11.00 ± 0.76 b | 10.35 ± 1.52 bc | 11.00 ± 1.20 b | 13.00 ± 2.08 b |
| Formulation C | 8.58 ± 2.36 b | 12.65 ± 1.15 bc | 4.00 ± 2.65 ab | 7.33 ± 2.18 ab |
| Formulation D | 7.25 ± 0.95 b | 5.00 ± 0.35 ab | 5.65 ± 0.55 ab | 6.65 ± 1.20 ab |

TABLE 15-continued

Effect of direct spray application and residues of *Clitoria ternatea* formulations on oviposition of green mirid adults on beans in the laboratory.

| Treatments | 0.5% v/v | 1.0% v/v | 1.5% v/v | 2.0% v/v |
|---|---|---|---|---|
| Water (control) | 12.42 ± 3.33 b | 20.65 ± 3.38 c | 11.65 ± 3.35 b | 12.65 ± 3.35 b |
| Level of significance | P < 0.0001 | P < 0.0009 | P < 0.005 | P < 0.01 |

Means between treatments within columns followed by the same letter are not significantly different (P > 0.05); Tukey-Kramer multiple comparison test.

EXAMPLE 16

Oviposition Deterrent Activity of *Clitoria Ternatea* on Green Mirid Adult Females on Beans in the Laboratory: Days after Treatment and Adult Female Egg Lay The *Clitoria ternatea* formulations Formulation C, Formulation D and Formulation A were evaluated at 1 and 2 L/ha in the laboratory with 25° C. temperature and 40-55% RH. Water was used as control. For each formulation, a total of 6 adult mirid females and males (3 pairs) per treatment (1 pair/replicate) were sprayed on a filter paper until run off. Three beans were dipped for 60 seconds in each treatment or formulation. Each mirid pair and a treated bean from each treatment were transferred and kept separately in 35 mL clear plastic containers (P101M; Solo, Urbana, Illionis, USA). Each treatment was replicated 3 times. The numbers of green mirid eggs laid per female in each treatment were counted under a binocular microscope on 3, 5, 7, 9 and 11 days after treatment. The number of eggs per female per treatment were calculated and compared among treatments and control.

Results

Green mirid adult females did not lay any eggs on beans treated with 2 L/ha Formulation A at 3 to 11 DAT (Table 16). Beans treated with 1 L/ha Formulation A had no eggs recorded on them at 3 DAT but at 5 to 11 DAT the number of eggs recorded on the 1 L/ha Formulation A treated beans ranged from 0.67 to 2.00 per female (Table 16). The number of eggs laid on the on beans treated with 1 L/ha Formulation C, Formulation D and water at 3 DAT were 0.33, 0.67 and 2.00 per female respectively (Table 16). At the same period no eggs were recorded on beans treated with 2 L/ha Formulation C and Formulation D respectively (Table 16). At 5 DAT the beans treated with 1 L/ha Formulation C and Formulation D had 10 and 8.67 eggs/female respectively and the control had 5.33 per female. When the application rate of Formulation C and Formulation D were doubled to 2 L/ha, the number of eggs laid per female reduced to 4.00 (Formulation C) and 6.00 (Formulation D) and this was significantly different (P<0.01) from the 1 L/ha rate (Table 16). At 7 to 11 DAT, the number of eggs laid on beans treated with 2 L/ha Formulation C and Formulation D were not significantly different (P>0.05) from the 1 L/ha rate and the control (Table 16).

TABLE 16

Effect of *Clitoria ternatea* on the number of eggs laid by green mirid adult females in the laboratory

| Treatments | Pre-treatment | 3 DAT No. eggs laid/female | 5 DAT No. eggs laid/female | 7 DAT No. eggs laid/female | 9 DAT No. eggs laid/female | 11 DAT No. eggs laid/female |
|---|---|---|---|---|---|---|
| 1 L/ha Formulation C | 0 | 0.33 ± 0.33a | 10.00 ± 4.91a | 7.33 ± 0.67a | 8.67 ± 2.03a | 7.00 ± 1.37a |
| 1 L/ha Formulation D | 0 | 0.67 ± 0.33a | 8.67 ± 0.88a | 10.33 ± 0.8a | 10.67 ± 1.21a | 8.87 ± 1.21a |
| 1 L/ha Formulation A | 0 | 0 a | 0.67 ± 0.33 c | 2.00 ± 1.00b | 2.00 ± 1.00 b | 1.07 ± 1.00bc |
| 2 L/ha Formulation C | 0 | 0 a | 4.00 ± 2.00 b | 7.00 ± 1.85a | 6.33 ± 1.67a | 4.53 ± 2.03ab |
| 2 L/ha Formulation D | 0 | 0 a | 6.00 ± 3.79 b | 5.67 ± 0.57ab | 4.67 ± 1.45ab | 4.27 ± 0.97ab |
| 2 L/ha Formulation A | 0 | 0 a | 0 c | 0 b | 0 b | 0 c |
| Control (water) | 0 | 2.00 ± 1.16a | 5.33 ± 2.67ab | 9.67 ± 2.85a | 8.00 ± 0.58a | 7.13 ± 0.58a |
| Level of significance | | P < 0.0001 | P < 0.01 | P < 0.01 | P < 0.01 | P < 0.05 |

Means between treatments within columns followed by the same letter are not significantly different (P > 0.05); Tukey-Kramer multiple comparison test.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

EXAMPLE 17

Efficacy of *Clitoria ternatea* Formulations Against Cotton Pests

The trial was conducted in an irrigated commercial conventional cotton crops at the Australian Cotton Research Institute farm in Narrabri. A sunflower strip was planted on one side of the field to generate high densities of green mirids and other cotton pests and beneficial insects.

The following treatments were evaluated against cotton pests especially green mirids: (1) 1 L/ha Formulation C, (2) 1 L/ha Formulation D, (3) 1 L/ha Formulation A, (4) 1 L/ha Formulation B, (5) Conventional insecticides (62.5 ml/ha Fipronil and 0.80 L/ha Steward) and (6) Unsprayed (untreated) control. The treatment plots were arranged in a randomised complete block design with 4 replicates per treatment. Each replicated plot measured 8 m wide and 100 meters long.

Foliar applications of each treatment were made over a period of 3 months. The decision to apply the treatment was made based on the IPM Guidelines and CottonLogic recommended economic threshold of 0.5 green mirids per meter. In all, 3 applications of each treatment were applied throughout the season.

Pre-treatment counts were made visually of green mirid adults and nymphs, green vegetable bugs, non target arthropods such as apple dimpling bugs, *thrips*, jassids and aphids on cotton plants. Post-treatment counts were made on 3, 7 and 14 days after treatment application. In each counts, two randomly selected 2 meter lengths of row of each treatment replicate, i.e. a total of 8 meters were examined per treatment. Data were expressed as numbers per meter for each treatment for each spray application and number per meter per sample date at the end of the season.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

Results

Efficacy of *Clitoria ternatea* Oil Based Formulations on *Helicoverpa* Spp. in Commercial Cotton Approximately equal number of *Helicoverpa* spp. eggs per meter per sample date were found on plots treated with conventional insecticide (2.22±0.26) compared with 1.64, 1.71 and 1.57 on 1 L/ha Formulation C (1.64), 1 L/ha Formulation D (1.71) and 1 L/ha Formulation A (Table 17). The number of *Helicoverpa* eggs per meter per sample date found on the plots treated with 1 L/ha Formulation B (formulation without *Clitoria ternatea* i.e. *Clitoria ternatea* carrier) was significantly higher (P<0.0001) than the other *Clitoria ternatea* formulations but was the same as plots treated with conventional insecticides (Table 17). The unsprayed plot (3.90 per meter) recorded the highest number of *Helicoverpa* eggs per meter per sample date than all the other treatments (Table 17). The mortalities of eggs on the conventional insecticide treated plots (43.1%) was significantly lower (P<0.001) than the Formulation C (58.0%), Formulation D (56.2%) and Formulation A (59.7%)—treated plots (Table 1). The Formulation B treated plots had 26.2% mortalities of *Helicoverpa* spp. eggs (Table 17).

The number of VS+S larvae was the same in conventional insecticide (1.19) compared with 1.70, 1.65 and 1.46 On the Formulation C (1.70), Formulation D (1.65) and Formulation A (1.46) treated plots (Table 17). Plots treated with Formulation B had significantly higher (P<0.0001) number of *Helicoverpa* spp. VS+S larvae than the other plots treated with the other *Clitoria ternatea* formulations and conventional insecticide (Table 17). The unsprayed plot had the highest number of VS+S larvae among the treatments but this was not significantly different (P>0.05) from the Formulation B treated plots (Table 17). The mortalities of VS+S larvae on the conventional insecticide treated plots (53.9%) was higher than the Formulation C (34.1%), Formulation D (36.1%) and Formulation A (43.4%) (Table 17). The mortality of VS+S larvae on the Formulation B (10.1%) treated plots was the lowest among the *Clitoria ternatea* formulations.

The number of *Helicoverpa* spp. M+L larvae found on the conventional insecticide plots (0.30) was the same as the Formulation C (0.45), Formulation D (0.46) and Formulation A (0.26) treated plots (Table 17). The number of M+L larvae per meter per sample date found on the Formulation B treated plots (0.70) was the same as the unsprayed plots but significantly higher than the other *Clitoria ternatea* formulations (Table 17). The mortalities of M+L larvae on the conventional insecticide plots (68.1%) were lower than the Formulation A treated plots (73.3%). The mortalities of M+L larvae on plots treated with Formulation C (52.1%) and Formulation D (51.1%) was lower than Formulation A plots (73.3%) but higher than Formulation B treated plots (25.5%) (Table 17).

TABLE 17

Overall effect of *Clitoria ternatea* extracts on *Helicoverpa* spp. eggs, very small and small larvae and medium and large larvae on commercial conventional cotton crops

| Treatments | *Helicoverpa* eggs/metre/ sample date (% mortality) | *Helicoverpa* VS + S larvae/metre/ sample date (% mortality) | *Helicoverpa* M + L/metre/ sample date (% mortality) |
|---|---|---|---|
| 1 L/ha Formulation C | 1.64 ± 0.26 a (58.0%) | 1.70 ± 0.22 a (34.1%) | 0.45 ± 0.11 a (52.1%) |
| 1 L/ha Formulation D | 1.71 ± 0.26 a (56.2%) | 1.65 ± 0.25 a (36.1%) | 0.46 ± 0.10 a (51.1%) |
| 1 L/ha Formulation A | 1.57 ± 0.24 a (59.7%) | 1.46 ± 0.21 a (43.4%) | 0.26 ± 0.06 a (73.3%) |
| 1 L/ha Formulation B | 2.88 ± 0.23 b (26.2%) | 2.32 ± 0.25 bc (10.1%) | 0.70 ± 0.13 bc (25.5%) |
| Conventional | 2.22 ± 0.26 ab (43.1%) | 1.19 ± 0.20 a (53.9%) | 0.30 ± 0.06 a (68.1%) |
| Unsprayed (Control) | 3.90 ± 0.33 c (0) | 2.58 ± 0.29 c (0) | 0.94 ± 0.19 c (0) |
| Level of significance | P < 0.0001 | P < 0.0001 | P < 0.0001 |

Means between treatments within columns followed by the same letter are not significantly different (P > 0.05); Tukey-Kramer multiple comparison test.

EXAMPLE 18

Efficacy of *Clitoria ternatea* Oil Based Formulations on Sucking Pests on Commercial Cotton Green Mirids The number of green mirids per meter per sample date was the same in conventional insecticide (0.33) compared with 1.07, 1.09 and 0.77 on the Formulation C (1.07), Formulation D (1.09) and Formulation A (0.77) treated plots (Table 18). Plots treated with Formulation B had significantly higher (P<0.0001) number of green mirids per meter per sample date than the other plots treated with the *Clitoria ternatea* formulations and conventional insecticide (Table 18). The unsprayed plot had the highest number of green mirids per meter per sample date among all treatments but was not significantly different (P>0.05) from the Formulation B treated plots (Table 18). The mortalities of green mirids on the conventional insecticide treated plots (81.5%) was higher than the Formulation C (39.9%), Formulation D (38.8%) and Formulation A (56.7%) (Table 18). The mortality of green mirids on the Formulation B—treated plots (32.6%) was the lowest among the *Clitoria ternatea* formulations (Table 18).

Green Vegetable Bugs

The number of green vegetable bugs per meter per sample date was the same in conventional insecticide (0.19) compared with 0.44, 0.35 and 0.17 on the Formulation C (0.44), Formulation D (0.35), Formulation A (0.17) and Formulation B (0.54) treated plots (Table 18). Plots treated with Formulation B (0.54) had significantly higher (P<0.0001) number of green vegetable bugs per meter per sample date than the other plots treated with the *Clitoria ternatea* formulations and conventional insecticide (Table 18). The unsprayed plot had the highest number of green vegetable bugs per meter per sample date among all treatments but was not significantly different (P>0.05) from the Formulation B treated plots (Table 18). The mortalities of green vegetable bugs on the conventional insecticide treated plots (81.5%) was higher than the Formulation C (39.9%), Formulation D (38.8%) and Formulation A (56.7%) (Table 18). The mortality of green vegetable bugs on the Formulation B—treated plots (32.6%) was the lowest among the *Clitoria ternatea* formulations (Table 18).

Aphids

Approximately equal number of cotton aphids per meter per sample date were found on plots treated with conventional insecticide (1.20) compared with 2.09, 2.06, 0.17 and 2.62 on the Formulation C (2.09), Formulation D (2.06), Formulation A (1.36) and Formulation B (2.62) treated plots (Table 18). Plots treated with Formulation B (2.62) had significantly higher (P<0.0001) number of cotton aphids per meter per sample date than the other plots treated with the *Clitoria ternatea* formulations and conventional insecticide (Table 18). The unsprayed plot had the highest number of cotton aphids per meter per sample date among all treatments but was not significantly different (P>0.05) from the Formulation B treated plots (Table 18). The mortalities of cotton aphids on the conventional insecticide treated plots (63.4%) was higher than the Formulation C (36.3%), Formulation D (37.2%) and Formulation A (58.5%) (Table 18). The mortality of aphids on the Formulation B—treated plots (20.1%) was the lowest among the *Clitoria ternatea* formulations (Table 18).

TABLE 18

Efficacy of *Clitoria ternatea* extracts on green mirids, green vegetable bugs and cotton aphids in commercial cotton crops

| Treatments | No. Green mirids/metre/ sample date (% mortality) | No. Green vege bug/metre/ sample date (% mortality) | No. Aphids/ metre/ sample date (% mortality) |
|---|---|---|---|
| 1 L/ha Formulation C | 1.07 ± 0.19 a (39.9%) | 0.44 ± 0.09 ab (47.6%) | 2.09 ± 0.57 a (36.3%) |
| 1 L/ha Formulation D | 1.09 ± 0.18 a (38.8%) | 0.35 ± 0.11 ab (58.3%) | 2.06 ± 0.40 a (37.2%) |
| 1 L/ha Formulation A | 0.77 ± 0.14 ab (56.7%) | 0.17 ± 0.07 a (79.8%) | 1.36 ± 0.29 a (58.5%) |
| 1 L/ha Formulation B | 1.20 ± 0.21 ac (32.6%) | 0.54 ± 0.14 bc (35.7%) | 2.62 ± 1.07 a (20.1%) |
| Conventional | 0.33 ± 0.11 b (81.5%) | 0.19 ± 0.07 a (77.4%) | 1.20 ± 0.27 a (63.4%) |
| Unsprayed (Control) | 1.78 ± 0.25 c (0) | 0.84 ± 0.18 c (0) | 3.28 ± 0.53 a (0) |
| Level of significance | P < 0.0001 | P < 0.0001 | P > 0.05 |

Means between treatments within columns followed by the same letter are not significantly different (P > 0.05); Tukey-Kramer multiple comparison test.

Apple Dimpling Bugs

The number of apple dimpling bugs per meter per sample date found on plots treated with conventional insecticide (2.03) were lower than those on plots treated with Formulation C (3.59), Formulation D (3.88), Formulation A (2.70) and Formulation B (4.32) (Table 19). Plots treated with Formulation B (4.32) had significantly higher (P<0.0001) number of Apple dimpling bugs per meter per sample date than the other plots treated with the *Clitoria ternatea* formulations and conventional insecticide (Table 19). The unsprayed plot (4.57) had the highest number of Apple dimpling bugs per meter per sample date among all treatments but was not significantly different (P>0.05) from the Formulation B treated plots (Table 19). The mortalities of Apple dimpling bugs on the conventional insecticide treated plots (55.6%) was higher than the Formulation C (21.4%), Formulation D (15.1%) and Formulation A (40.9%) (Table 19). The mortality of Apple dimpling bugs on the Formulation B—treated plots (5.5%) was the lowest among the *Clitoria ternatea* formulations (Table 19).

Green Jassids

The number of green jassids per meter per sample date found on plots treated with conventional insecticide (2.03) was the same as those found on plots treated with Formulation C (2.93), Formulation D (2.88), Formulation A (2.16) and Formulation B (3.13) treated plots (Table 19). Plots treated with Formulation A (2.16) had significantly lower (P<0.0002) number of green jassids per meter per sample date than the plots treated with Formulation B (3.13). Plots treated with Formulation B had the same number of green jassids per meter per sample date than plots treated with Formulation C, Formulation D and the unsprayed plot (3.78) (Table 19). The survival rates of green jassids on the conventional insecticide treated plots (28.6%) were lower than plots treated with Formulation A (42.9%). The mortalities of green jassids on the Formulation C and Formulation D treated were approximately the same as plots treated with Formulation B (17.2) (Table 19).

Thrips

Approximately equal number of *thrips* per meter per sample date were found on plots treated with conventional insecticide (11.06) compared with Formulation C (10.00), Formulation D (10.19), Formulation A (10.62), Formulation B (11.04) treated plots and the control plots (12.22) (Table 19). Plots treated with Formulation A (10.62) had the same number of *thrips* per meter per sample date as plots treated with Formulation B (11.04). Plots treated with both Formulation A and Formulation B had the same number of *thrips* per meter per sample date as plots treated with Formulation C, Formulation D, conventional insecticides and unsprayed plot (12.22) (Table 19). The mortalities of *thrips* on the conventional insecticide treated plots (9.5%) were the same as plots treated with the *Clitoria ternatea* formulations Formulation A (Table 19).

TABLE 19

Efficacy of *Clitoria ternatea* extracts on apple dimpling bugs, green jassids and thrips in commercial cotton crops

| Treatments | No. Apple Dimpling bug/metre/ sample date (% mortality) | No. Green jassids/ metre/ sample date (% mortality) | No. Thrips/ metre/ sample date (% mortality) |
|---|---|---|---|
| 1 L/ha Formulation C | 3.59 ± 0.53 ab (21.4%) | 2.93 ± 0.32 abc (22.5%) | 10.00 ± 1.13 a (18.2%) |
| 1 L/ha Formulation D | 3.88 ± 0.52 a (15.1%) | 2.88 ± 0.33 ac (23.8%) | 10.19 ± 1.21 a (16.6%) |
| 1 L/ha Formulation A | 2.70 ± 0.46 bc (40.9%) | 2.16 ± 0.22 b (42.9%) | 10.62 ± 1.12 a (13.1%) |
| 1 L/ha Formulation B | 4.32 ± 0.62 a (5.5%) | 3.13 ± 0.29 ac (17.2%) | 11.04 ± 1.08 a (9.7%) |
| Conventional | 2.03 ± 0.33 c (55.6%) | 2.70 ± 0.31 ab (28.6%) | 11.06 ± 1.25 a (9.5%) |

TABLE 19-continued

Efficacy of *Clitoria ternatea* extracts on apple dimpling bugs, green jassids and thrips in commercial cotton crops

| Treatments | No. Apple Dimpling bug/metre/ sample date (% mortality) | No. Green jassids/ metre/ sample date (% mortality) | No. Thrips/ metre/ sample date (% mortality) |
|---|---|---|---|
| Unsprayed (Control) | 4.57 ± 0.56 a (0) | 3.78 ± 0.36 c (0) | 12.22 ± 1.44 a (0) |
| Level of significance | P < 0.0001 | P < 0.0002 | P > 0.33 |

Means between treatments within columns followed by the same letter are not significantly different (P > 0.05); Tukey-Kramer multiple comparison test.

EXAMPLE 19

Efficacy of *Clitoria ternatea* Formulations Against Key Beneficial Insects

The trial was conducted in an irrigated commercial conventional cotton crops at the Australian Cotton Research Institute farm in Narrabri. A sunflower strip was planted on one side of the field to generate high densities of green mirids and other cotton pests and beneficial insects.

The following *Clitoria ternatea* formulations were evaluated against beneficial insects on cotton crops (1) 1 L/ha Formulation C, (2) 1 L/ha Formulation D, (3) 1 L/ha Formulation A, (4) 1 L/ha Formulation B, (5) Conventional insecticides (62.5 ml/ha Fipronil and 0.80 L/ha Steward) and (6) Unsprayed (untreated) control. The treatment plots were arranged in a randomised complete block design with 4 replicates per treatment. Each replicated plot measured 8 m wide and 100 meters long.

Foliar applications of each treatment were made over 3 months. The decision to apply the treatment was made based on the IPM Guidelines and CottonLogic recommended predator to pre ratio of 0.5. In all, 3 applications of each treatment were applied throughout the season.

Pre-treatment counts were made visually of beneficial insects such as predatory beetles, predatory bugs, predatory lacewings and spiders on cotton plants. Post-treatment counts were made on 3, 7 and 14 days after treatment application. In each counts, two randomly selected 2 meter lengths of row of each treatment replicate, i.e. a total of 8 meters were examined per treatment. Data were expressed as numbers per meter for each treatment for each spray application and number per meter per sample date for each treatment at the end of the season.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

Results

Predatory insects identified from the treated plots were predatory beetles, bugs, lacewings and spiders (see Table 7).

Predatory Beetles

No significant difference (P>0.05) in the number of predatory beetles per meter per sample date were recorded in plots treated with the *Clitoria ternatea* formulations and the control (unsprayed) plots (Table 20). However, significant differences were found between plots treated with conventional insecticides and plots treated with *Clitoria ternatea* formulations (Table 20). Plots treated with conventional insecticides had 1.51 predatory beetles per meter per sample date compared with 2.25, 2.19, 2.00, 2.20 and 2.51 for Formulation C (2.25), Formulation D (2.19), Formulation A (2.00), Formulation B (2.20) and control (2.51) plots (Table 20).

Predatory Bugs

The highest number of predatory bugs per meter per sampling date was recorded on the Control plots (1.78) but this was not significantly different (P>0.05) from plots treated with Formulation B (1.65), Formulation A (1.25), Formulation C (1.16) and Formulation D (1.25) (Table 20). The conventional insecticide-treated cotton crops had the least number of predatory bugs (P<0.0001) (Table 20).

Predatory Lacewings

No significant difference (P>0.05) in the number of predatory lacewings per meter per sampling were found on plots treated with *Clitoria ternatea* formulations and the conventional insecticide treated plots (Table 20). The highest number of lacewings per meter was recorded in the unsprayed plot (1.01) but was not significantly different (P>0.05) from the plots treated with the *Clitoria ternatea* formulations (Table 20). In contrast the least number of lacewings per meter was recorded on the conventional insecticide treated plots and this was significantly different (P<0.03) from the control plots (Table 20).

Spiders

The number of spiders per meter per sampling date were recorded on the unsprayed (control) plots (3.28) compared with 2.52, 3.10, 2.78, 2.73 and 2.13 on the Formulation C (2.52), Formulation D (3.10), Formulation A (2.78), Formulation B (2.73) and the conventional insecticide (2.13) plots (Table 20). The difference between the spider numbers per meter per sample date found on the control plots was not significantly different (P>0.05) from plots treated with *Clitoria ternatea* formulations but was different (P<0.0003) from the conventional insecticide treated plots (Table 20). The number of spiders recorded on the conventional insecticide treated plots was not significantly different (P>0.05) from plots treated with *Clitoria ternatea* formulations exception is Formulation D treated plots (Table 20).

TABLE 20

Effect of *Clitoria ternatea* extracts on predatory insects on commercial conventional cotton crops

| Treatments | No. Predatory beetles/metre/ sample date | No. Predatory bugs/metre/ sample date | No. Predatory lacewings/metre/ sample date | No. Spiders/ metre/ sampling date |
|---|---|---|---|---|
| 1 L/ha Formulation C | 2.25 ± 0.19 a | 1.16 ± 0.19 ab | 0.73 ± 0.10 ab | 2.52 ± 0.21 ab |
| 1 L/ha Formulation D | 2.19 ± 0.17 a | 1.38 ± 0.22 ab | 0.86 ± 0.13 ab | 3.10 ± 0.22 a |

TABLE 20-continued

Effect of *Clitoria ternatea* extracts on predatory
insects on commercial conventional cotton crops

| Treatments | No. Predatory beetles/metre/ sample date | No. Predatory bugs/metre/ sample date | No. Predatory lacewings/metre/ sample date | No. Spiders/ metre/ sampling date |
|---|---|---|---|---|
| 1 L/ha Formulation A | 2.00 ± 0.19 a | 1.25 ± 0.18 ab | 0.99 ± 0.14 ab | 2.78 ± 0.25 ab |
| 1 L/ha Formulation B | 2.20 ± 0.21 a | 1.65 ± 0.21 b | 0.74 ± 0.11 ab | 2.73 ± 0.24 ab |
| Conventional | 1.51 ± 0.17 b | 0.97 ± 0.17 a | 0.58 ± 0.98 a | 2.13 ± 0.19 b |
| Unsprayed (Control) | 2.51 ± 0.18 a | 1.78 ± 0.26 b | 1.01 ± 0.14 b | 3.28 ± 0.30 a |
| Level of significance | P < 0.001 | P < 0.001 | P < 0.03 | P < 0.0003 |

Means between treatments within columns followed by the same letter are not significantly different (P > 0.05); Tukey-Kramer multiple comparison test.

EXAMPLE 20

Efficacy of *Clitoria ternatea* Formulations on Silverleaf Whiteflies

The following *Clitoria ternatea* formulations were used in the trials to determine the efficacy of the *Clitoria ternatea* product against *Bemisia tabaci*—b-biotype (silverleaf whitefly) adults and nymphs: They are
(1) Formulation A (*Clitoria ternatea* formulation in oil without emulsifiers),
(2) Formulation D (*Clitoria ternatea* formulations with emulsifiers)
Effect of *Clitoria ternatea* Extracts on *Bemisia tabaci* on Commercial Cotton Crops at Merah North Near Wee Waa The trial was conducted in an irrigated conventional cotton crops in a commercial cotton farm at Merah north near Wee Waa. Two trials were conducted for a two week period. The treatments evaluated were (1) 2 L/ha Formulation A (2) 2 L/ha Formulation D (3) Unsprayed (untreated) control. The treatment plots were arranged in a randomised complete block design with 3 replicates per treatment. Each replicated plot measured 24 m wide 100 m long.

Foliar applications of each treatment were made on day 1. Pre-treatment counts were made visually of *B. tabaci* adults and nymphs, on the under-surface of leaves of cotton plants in each treatment. Post-treatment counts were made on 3, 7 and 14 days after treatment application. In each sampling date, twenty (20) plants from each treatment replicate were randomly selected and *B. tabaci* adults on a leaf from the 5th node below the terminal of each plant (during the early morning hours (9-10 am) were counted visually by carefully turning the leaf over and counting the number of individual adults present.

In the case of nymphs, one leaf from the 5th node below the terminal of each of the 20 plants was cut, removed and carefully placed individually in a plastic bag. The plastic bags containing individual leaves were brought to the laboratory and the *B. tabaci* nymphs were counted under a binocular microscope. Data of both adults and nymphs were expressed as numbers per leaf for each treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

Results

The *B. tabaci* strains present in the study site were predominantly the b-biotype. The number of *B. tabaci* adults per leaf recorded in plots treated with Formulation A and Formulation D were significantly lower (P<0.01 on 3 DAT, P<0.05 on 7 DAT and P<0.0001 on 14 DAT) than the unsprayed plots (Table 21). The mortality of *B. tabaci* adults recorded on plots treated with 2 L/ha Formulation D on 3 DAT was 74.5% compared with 54.8 on 2 L/ha Formulation A treated plots (Table 21). However, on 7 and 14 DAT mortalities on Formulation A treated plots increased to 77.3 and 73.4% respectively whereas those on the Formulation D plots were 60.4 and 73.2% respectively relative to the control (Table 21).

In the case of *B. tabaci* nymphs per leaf, no significant difference (P>0.05) were found between plots treated with Formulation A and Formulation D but were significantly different (P<0.0001) from the unsprayed control on 3, 7 and 14 DAT (Table 22). However, the mortalities of *B. tabaci* nymphs on the Formulation D treated plots (74.9%) on 3 DAT were significantly higher than the Formulation A (28.2%) treated plots relative to the control (Table 22). On 7 and 14 DAT, mortalities recorded on the Formulation A treated plots increased to 73.6 and 55.6% whereas the mortality on the Formulation D treated plots were 75.3 and 67.0% respectively relative to the control (Table 22).

TABLE 21

Effect of *Clitoria ternatea* extracts on *Bemisia tabaci*
adults per leaf on commercial Bollgard cotton crops

| Treatments | Pre-treatment counts | 3 DAT (% mortality) | 7 DAT (% mortality) | 14 DAT (% mortality) |
|---|---|---|---|---|
| 2.0 L/ha Formulation A | 74.33 ± 6.15 a | 32.33 ± 3.90 a (54.8%) | 15.56 ± 1.70 a (77.3%) | 15.56 ± 1.70 a (73.4%) |
| 2.0 L/ha Formulation D | 70.89 ± 7.99 a | 18.22 ± 3.62 a (74.5%) | 27.11 ± 5.19 a (60.4%) | 15.67 ± 2.08 a (73.2%) |

TABLE 21-continued

Effect of *Clitoria ternatea* extracts on *Bemisia tabaci*
adults per leaf on commercial Bollgard cotton crops

| Treatments | Pre-treatment counts | 3 DAT (% mortality) | 7 DAT (% mortality) | 14 DAT (% mortality) |
|---|---|---|---|---|
| Unsprayed (Control) | 53.56 ± 7.51 a | 71.56 ± 8.85 b (0) | 68.45 ± 5.70 b (0) | 58.44 ± 5.82 b (0) |
| Level of significance | P > 0.05 | P < 0.001 | P < 0.05 | P < 0.0001 |

TABLE 22

Effect of *Clitoria ternatea* extracts and conventional insecticides on
*Bemisia tabaci* nymphs per leaf on commercial Bollgard cotton crops

| Treatments | Pre-treatment counts | 3 DAT | 7 DAT | 14 DAT |
|---|---|---|---|---|
| 2.0 L/ha Formulation A | 75.56 ± 11.35 a | 51.11 ± 8.08 a (28.2%) | 44.78 ± 7.15 a (73.6%) | 121.33 ± 15.91 a (55.6%) |
| 2.0 L/ha Formulation D | 75.56 ± 11.18 a | 17.89 ± 2.90 a (74.9%) | 41.78 ± 4.85 a (75.3%) | 90.11 ± 5.58 a (67.0%) |
| Unsprayed (Control) | 77.22 ± 9.06 a | 71.22 ± 8.35 b (0) | 169.33 ± 25.10 b (0) | 273.22 ± 24.21 b (0) |
| Level of significance | P > 0.05 | P < 0.0001 | P < 0.0001 | P < 0.0001 |

Means between treatments within columns followed by the same letter are not significantly different (P > 0.05); Tukey-Kramer multiple comparison test.

EXAMPLE 21

Effect of *Clitoria ternatea* Extracts and Conventional Insecticides on *Bemisia tabaci* on Commercial Cotton Crops The trial was conducted in an irrigated conventional cotton crops in a cotton farm. The following treatments were evaluated against *B. tabaci*—b-biotype adults and nymphs: (1) 2 L/ha Formulation A (2) 2 L/ha Formulation D (3) 0.80 L/ha Diafenthiuron at Merah north (conventional insecticides) and (4) Unsprayed (control). The treatment plots were arranged in a randomised complete block design with 3 replicates per treatment. Each replicated plot measured 24 m wide 100 m long.

Foliar applications of each treatment were made over two weeks. Pre-treatment counts were made visually of *B. tabaci* adults and nymphs, on the under-surface of leaves of cotton plants in each treatment. Post-treatment counts were made on 3, 7 and 14 days after treatment application. Data of both adults and nymphs were expressed as numbers per leaf for each treatment.

Analysis of the Data

All experimental data were analysed using repeated measures ANOVA (Graphpad Instat and Prism Software, Inc. v. 2.03, San Diego, Calif., USA). Treatment and sample dates were the independent variables. Tukey-Kramer Multiple comparisons tests were used to separate means.

Results

The *B. tabaci* strains present in the study site were predominantly the b-biotype. Approximately equal number of *B. tabaci* adults per leaf were found on plots treated with conventional insecticides (15.33) on 3 DAT compared with 18.00, 11.33 and 25.00 on Formulation D, Formulation A and unsprayed plots (Table 23). On 7 DAT, the number of adults per leaf recorded on Formulation A treated plots were the same as Formulation D and conventional insecticide plots but was significantly different (P<0.0001) from the control plots (Table 23). In contrast, the number of *B. tabaci* adults per leaf found on Formulation D and conventional insecticide plots were not significantly different (P>0.05) from the control plots (Table 23). On 14 DAT, no significant differences (P>0.05) were recorded among the treatments and control plots (Table 23). However, the mortalities of *B. tabaci* adults on the Formulation D treated plots (54.7%) on 3 DAT was higher than the Formulation A plots (28.0%) and conventional insecticide plots (38.7%) (Table 23). On 7 DAT, mortalities of *B. tabaci* adults (66.7%) was higher than the Formulation D (38.9%) and conventional insecticide (32.2%) relative to the control (Table 23). In contrast, the difference in mortality among treatments was approximately the same relative to the control on 14 DAT (Table 23).

The number of *B. tabaci* nymphs per leaf found on plots treated with Formulation A and Formulation D were not significantly different (P>0.05) but were significantly different (P<0.06) from the conventional insecticide and the unsprayed plots on 3 DAT (Table 24). No significance difference (P>0.05) was detected on 3 DAT between conventional insecticide treated and unsprayed plots (Table 24). No significant differences (P>0.05) were found among treatments and control on 7 DAT but a significant difference was found between *Clitoria ternatea* treated plots and the conventional and unsprayed plots (Table 24). In terms of mortalities, Formulation A and Formulation D treated plots recorded 53.3 and 36.4% mortalities of *B. tabaci* nymphs compared with conventional insecticide treated plots which recorded a 12 percent increase of nymphs over the control plot (Table 24). On 7 DAT, the Formulation D treated plots had 47.5 percent mortality compared with Formulation A (28.8%) and conventional insecticide (22.1%). On 14 DAT, the mortality caused individual treatments was increased to 77.2 percent (Formulation A), 79.5% (Formulation D) and 60.6% (conventional insecticides) (Table 24).

TABLE 23

Effect of *Clitoria ternatea* extracts and conventional insecticides on *Bemisia tabaci* adults per leaf on commercial Bollgard cotton crops

| Treatments | Pre-treatment counts | 3 DAT (% mortality) | 7 DAT (% mortality) | 14 DAT (% mortality) |
|---|---|---|---|---|
| 2.0 L/ha Formulation A | 24.33 ± 2.96 a | 18.00 ± 2.89 a (28.0%) | 10.00 ± 1.73 a (66.7%) | 14.67 ± 2.90 a (20.0%) |
| 2.0 L/ha Formulation D | 28.00 ± 3.51 a | 11.33 ± 0.88 a (38.9%) | 18.33 ± 5.04 ab (38.9%) | 12.33 ± 2.33 a (32.7%) |
| 0.80 L/ha Diafenthiuron | 25.67 ± 1.76 a | 15.33 ± 1.45 a (54.7%) | 20.33 ± 2.40 ab (32.2%) | 12.00 ± 0.88 a (34.5%) |
| Unsprayed (Control) | 23.00 ± 4.73 a | 25.00 ± 2.65 b (38.7%) | 30.00 ± 5.77 b (0) | 18.33 ± 2.33 a (0) |
| Level of significance | $P > 0.05$ | $P < 0.0001$ | $P < 0.0001$ | $P > 0.05$ |

Means between treatments within columns followed by the same letter are not significantly different ($P > 0.05$); Tukey-Kramer multiple comparison test.

TABLE 24

Effect of *Clitoria ternatea* extracts and conventional insecticides on *Bemisia tabaci* nymphs per leaf on commercial Bollgard cotton crops

| Treatments | Pre-treatment counts | 3 DAT (% mortality) | 7 DAT (% mortality) | 14 DAT (% mortality) |
|---|---|---|---|---|
| 2.0 L/ha Formulation A | 29.67 ± 5.78 a | 12.00 ± 1.00 a (53.3%) | 14.00 ± 3.06 a (28.8%) | 9.67 ± 2.19 a (77.2%) |
| 2.0 L/ha Formulation D | 38.00 ± 2.52 a | 16.33 ± 2.33 a (36.4%) | 10.33 ± 0.33 a (47.5%) | 8.67 ± 1.33 a (79.5%) |
| 0.80 L/ha Diafenthiuron | 40.00 ± 9.87 a | 28.67 ± 7.22 b (−12.0%) | 15.33 ± 2.40 a (22.1%) | 17.00 ± 1.73 b (60.6%) |
| Unsprayed (control) | 17.67 ± 3.33 a | 25.67 ± 7.22 b (0) | 19.67 ± 0.33 a (0) | 42.33 ± 3.93 b (0) |
| Level of significance | $P > 0.05$ | $P < 0.06$ | $P > 0.05$ | $P < 0.001$ |

Means between treatments within columns followed by the same letter are not significantly different ($P > 0.05$); Tukey-Kramer multiple comparison test.

REFERENCES

The disclosure of the following documents is incorporated herein by reference:

1 Bernays, E. A. and Chapman, R. F. (1994). Host Plant Selection by Phytophagous Insects. Chapman and Hall. London.
2 Mensah, R. K., Verneau, S. and Frerot, B. (2000). Deterrence of oviposition of adult *Ostrinia nubilalis* (Hubner) by a natural enemy food supplement Envirofeast® on maize in France. International Journal of Pest Management 46 (1), 49-53
3 Mensah, R. K. (1996). Suppression of *Helicoverpa* spp. oviposition by use of natural enemy food supplement "Envirofeast". Australian Journal of Entomology, 35, 323-329.
4 Mensah, R. and Moore, C. J. (1999). A Review of Behaviour Modifying Chemicals in Relation to Pest Host Selection and Management on Australian Cottons. CRDC.
5 Miller, J. R. and Cowles, R. S. (1990). Stimulo-deterrent diversion: a concept and its possible application to onion maggot control. J. Chem. Ecol. 16: 3197-3212.
6 Pyke, B., Rice, M., Sabine, G. and Zalucki, M. (1987). The push-pull strategy-behavioural control of *Heliothis*. Australian Cotton Grower 9: 7-9.
7 Rhoades, D. F. and Coates, R. H. (1976). Towards a general theory of plant anti-herbivore chemistry. In: J. W. Wallace and L. Mansell, eds. Biochemical Interactions Between Insects and Plants. Pp. 168-213. Plenum, New York.
8 Tingle, F. C. and Mitchell, E. R. (1984). Aqueous extracts from indigenous plants as oviposition deterrents for *Heliothis virescens*. J. Chem. Ecology 10: 101-113.

The invention claimed is:

1. A composition for controlling insect pests in the form of an emulsion and/or an emulsifiable concentrate, the composition comprising:
an extract from at least the leaf of *Clitoria ternatea* in a pre-flower stage comprising SPCs which have insecticidal activity and/or which repel the insect pest and/or deter the insect pest from laying eggs and/or influence the position of egg laying and/or deter the insect pest from feeding on a plant,
one or more emulsifiers, and
optionally a carrier,
wherein the composition is in the form of an emulsion and/or an emulsifiable concentrate.

2. A composition as claimed in claim 1 further comprising one or more agriculturally acceptable excipients.

3. A composition as claimed in claim 1 wherein the carrier is a non-polar solvent or an oil.

4. A composition as claimed in claim 3 wherein the oil is canola oil or cotton seed oil.

5. A composition as claimed in claim 1 wherein said extract from *Clitoria ternatea* is an extract in a polar solvent.

6. A composition as claimed in claim 5 wherein the polar solvent is an alcohol, ketone, aldehyde or sulfoxide.

7. A composition as claimed in claim 6 wherein the polar solvent is an alcohol.

8. A composition as claimed in claim 7 wherein the polar solvent is methanol.

9. A composition as claimed in claim 7 wherein the polar solvent is ethanol.

10. The composition as claimed in claim 1 wherein the extract is an extract of the leaf and one or more of a stem, a root, a pod, a seed or a combination of any of the parts of the *Clitoria ternatea* plant.

11. The composition as claimed in claim 1 wherein the extract is an extract of the whole plant of *Clitoria ternatea*.

12. The composition as claimed in claim 1 wherein the composition is in the form of an emulsion.

13. The composition as claimed in claim 1 wherein the composition is in the form of an emulsifiable concentrate.

14. A method of controlling one or more insect pests, the method comprising treating a locus with the composition of claim 1.

15. A method as claimed in claim 14 wherein said locus is a plant or crop suffering from an infestation of insect pests on a plant or crop prone to such infestation.

16. A method as claimed in claim 15 wherein the plant or crop is selected from the group consisting of cotton, a grain crop, a legume crop, a pulse crop, a vegetable crop and a fruit crop.

17. A method as claimed in claim 15 wherein the plant is an ornamental plant.

18. A method as claimed in claim 14 wherein the controlling of one or more insect pests is by reducing egg laying.

19. A method as claimed in claim 14 wherein the controlling of one or more insect pests is by deterrence of insect feeding.

20. A method as claimed in claim 14 wherein the controlling of one or more insect pests is by direct kill.

21. A method as claimed in claim 14 wherein said one or more insect pests is selected from the group consisting of cotton bollworm, native budworm, green mirids, aphids, green vegetable bugs, apple dimpling bugs, plaque *thrips*, tobacco *thrips*, onion *thrips*, cotton *thrips*, western flower *thrips*, whiteflies, two spotted mites and leaf hoppers.

22. A method as claimed in claim 14 wherein non-target insect species numbers are not significantly affected thereby conserving natural enemies of the insect pests to supplement control of insect infestation.

\* \* \* \* \*